(12) United States Patent
Lesser

(10) Patent No.: US 10,119,964 B2
(45) Date of Patent: Nov. 6, 2018

(54) MULTIPLEX ASSAY STRIP, BEADS, DEVICE AND METHOD

(71) Applicant: Digital Biotech, LLC, Ardmore, PA (US)

(72) Inventor: Raymond Lesser, Ardmore, PA (US)

(73) Assignee: Digital Biotech, LLC, Ardmore, PA (US)

( * ) Notice: Subject to any disclaimer, the term of this patent is extended or adjusted under 35 U.S.C. 154(b) by 519 days.

(21) Appl. No.: 14/848,822

(22) Filed: Sep. 9, 2015

(65) Prior Publication Data

US 2016/0178624 A1 Jun. 23, 2016

Related U.S. Application Data

(60) Provisional application No. 62/095,336, filed on Dec. 22, 2014.

(51) Int. Cl.
*G01N 33/543* (2006.01)
(52) U.S. Cl.
CPC . *G01N 33/54313* (2013.01); *G01N 33/54366* (2013.01)
(58) Field of Classification Search
CPC .................. G01N 33/54313; G01N 33/54366
See application file for complete search history.

(56) References Cited

U.S. PATENT DOCUMENTS 3,932,141 A 1/1976 Beall et al.
4,659,222 A * 4/1987 Ekholm ................ B01L 3/5085
356/244
4,891,321 A * 1/1990 Hubscher ........... G01N 33/5302
422/404
4,935,208 A * 6/1990 Kohler ..................... B01L 9/52
206/558

(Continued)

FOREIGN PATENT DOCUMENTS

EP 24174 A1 2/1981

OTHER PUBLICATIONS

Int'l Search Report and Written Opinion dated Dec. 17, 2015 in Int'l Application No. PCT/US2015/050849.
WHO: "WHO Prequalification of In Vitro Diagnostics Programme. Public Report. Product: ImmunoComb® II HIV 1&2", Dec. 8, 2014, World Health Organization, Geneva, pp. 1-12.
Woodley Equipment Company: "Immunocomb Vaccicheck" In: "Immunocomb Vaccicheck," Oct. 1, 1989, Woodley Equipment Company, Bolton UK, XP055233158, pp. 1-3.

(Continued)

*Primary Examiner* — Melanie Yu Brown
(74) *Attorney, Agent, or Firm* — Panitch Schwarze Belisario & Nadel LLP

(57) ABSTRACT

A device termed the MobileArray™ device and methods, which form the MobileArray™ system, are disclosed for performing multiplex assays, target enrichment or purification. The device and methods disclosed enable the performing of multiplex assays, target enrichment or purification in a simplified manner. The MobileArray™ device gains the advantages and applications of the advanced multiplexing platforms, but does not require the special expensive equipment, reagents, software or dedicated operators. In addition, the MobileArray™ system can also be utilized in immunoprecipitation and target enrichment or purification in a (Continued)

multiplex manner. Furthermore, the MobileArray™ system can be integrated in an automated procedure. The MobileArray™ system makes it possible to apply multiplexing protocols in routine clinical practice, food safety inspection and general life science research laboratories.

9 Claims, 14 Drawing Sheets

(56) References Cited

U.S. PATENT DOCUMENTS

| | | | |
|---|---|---|---|
| 6,396,995 B1* | 5/2002 | Stuelpnagel | G01N 21/253 385/115 |
| 2004/0043398 A1* | 3/2004 | Sanchez-Martinez | G01N 33/543 435/6.11 |
| 2004/0241877 A1* | 12/2004 | Price | G01N 33/558 436/514 |

OTHER PUBLICATIONS

Rush et al, "Solid-Phase Radioimmunoassay on Polystyrene Beads and Its Application to Dopamine-β-Hydroxylase," Clinical Chemistry, vol. 21, No. 1, pp. 148-150 (1975).
Ziola et al, "Polystyrene Balls as the Solid-Phase of a Double Antibody Radioimmunoassay for Human Serum Albumin," Journal of Immunological Methods, vol. 17, pp. 309-317 (1977).
Fulton et al, "Advanced multiplexed analysis with the FlowMetrixTM system," Clinical Chemistry, vol. 43, No. 9, pp. 1749-1756 (1997).
Written Opinion dated Apr. 25, 2016 in Int'l Application No. PCT/US2015/050849.
Corrected Int'l Preliminary Report on Patentability dated Feb. 21, 2017, Corrected Mar. 3, 2017 in Int'l Application No. PCT/US2015/050849.
Int'l Preliminary Report on Patentability dated Jul. 13, 2016 in Int'l Application No. PCT/US2015/050849.

* cited by examiner

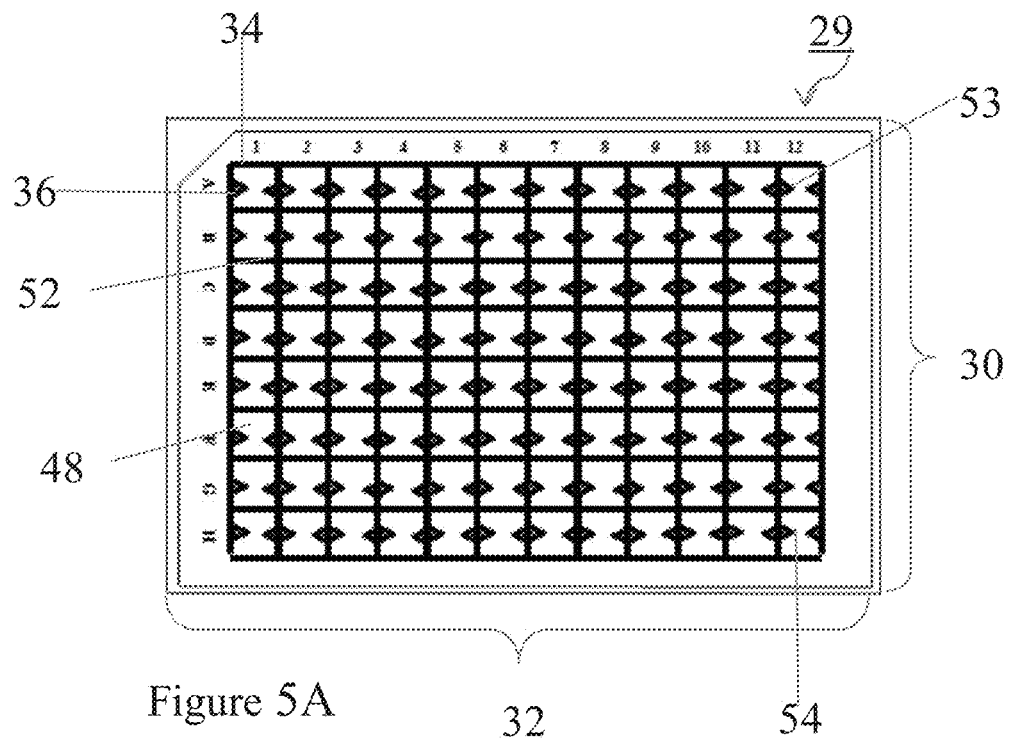
Figure 5A
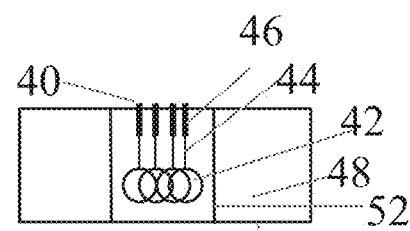
Figure 5B
Figure 5C
Figure 5D
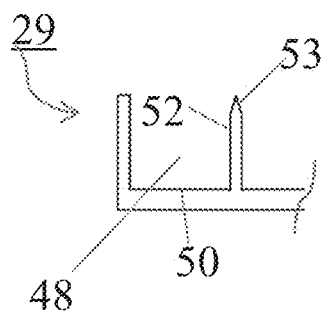
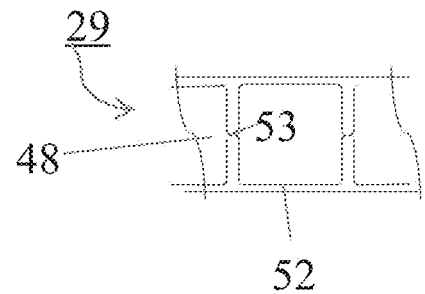

Incubation with 4 plex Figure 14A

|   | 1  | 2  | 3  | 4  | 5  | 6  | 7   | 8   | 9   | 10  | 11  | 12  |
|---|----|----|----|----|----|----|-----|-----|-----|-----|-----|-----|
| A | S1 | S1 | S1 | C1 | C1 | C1 | X7  | X7  | X7  | X15 | X15 | X15 |
| B | S2 | S2 | S2 | C2 | C2 | C2 | X8  | X8  | X8  | X16 | X16 | X16 |
| C | S3 | S3 | S3 | X1 | X1 | X1 | X9  | X9  | X9  | X17 | X17 | X17 |
| D | S4 | S4 | S4 | X2 | X2 | X2 | X10 | X10 | X10 | X18 | X18 | X18 |
| E | S5 | S5 | S5 | X3 | X3 | X3 | X11 | X11 | X11 | X19 | X19 | X19 |
| F | S6 | S6 | S6 | X4 | X4 | X4 | X12 | X12 | X12 | X20 | X20 | X20 |
| G | S7 | S7 | S7 | X5 | X5 | X5 | X13 | X13 | X13 | X21 | X21 | X21 |
| H | B  | B  | B  | X6 | X6 | X6 | X14 | X14 | X14 | X22 | X22 | X22 |

Detection Figure 14B

Analyte 1

|   | 1  | 2  | 3  | 4  | 5  | 6  | 7   | 8   | 9   | 10  | 11  | 12  |
|---|----|----|----|----|----|----|-----|-----|-----|-----|-----|-----|
| A | S1 | S1 | S1 | C1 | C1 | C1 | X7  | X7  | X7  | X15 | X15 | X15 |
| B | S2 | S2 | S2 | C2 | C2 | C2 | X8  | X8  | X8  | X16 | X16 | X16 |
| C | S3 | S3 | S3 | X1 | X1 | X1 | X9  | X9  | X9  | X17 | X17 | X17 |
| D | S4 | S4 | S4 | X2 | X2 | X2 | X10 | X10 | X10 | X18 | X18 | X18 |
| E | S5 | S5 | S5 | X3 | X3 | X3 | X11 | X11 | X11 | X19 | X19 | X19 |
| F | S6 | S6 | S6 | X4 | X4 | X4 | X12 | X12 | X12 | X20 | X20 | X20 |
| G | S7 | S7 | S7 | X5 | X5 | X5 | X13 | X13 | X13 | X21 | X21 | X21 |
| H | B  | B  | B  | X6 | X6 | X6 | X14 | X14 | X14 | X22 | X22 | X22 |

Analyte 2

|   | 1  | 2  | 3  | 4  | 5  | 6  | 7   | 8   | 9   | 10  | 11  | 12  |
|---|----|----|----|----|----|----|-----|-----|-----|-----|-----|-----|
| A | S1 | S1 | S1 | C1 | C1 | C1 | X7  | X7  | X7  | X15 | X15 | X15 |
| B | S2 | S2 | S2 | C2 | C2 | C2 | X8  | X8  | X8  | X16 | X16 | X16 |
| C | S3 | S3 | S3 | X1 | X1 | X1 | X9  | X9  | X9  | X17 | X17 | X17 |
| D | S4 | S4 | S4 | X2 | X2 | X2 | X10 | X10 | X10 | X18 | X18 | X18 |
| E | S5 | S5 | S5 | X3 | X3 | X3 | X11 | X11 | X11 | X19 | X19 | X19 |
| F | S6 | S6 | S6 | X4 | X4 | X4 | X12 | X12 | X12 | X20 | X20 | X20 |
| G | S7 | S7 | S7 | X5 | X5 | X5 | X13 | X13 | X13 | X21 | X21 | X21 |
| H | B  | B  | B  | X6 | X6 | X6 | X14 | X14 | X14 | X22 | X22 | X22 |

Analyte 3

|   | 1  | 2  | 3  | 4  | 5  | 6  | 7   | 8   | 9   | 10  | 11  | 12  |
|---|----|----|----|----|----|----|-----|-----|-----|-----|-----|-----|
| A | S1 | S1 | S1 | C1 | C1 | C1 | X7  | X7  | X7  | X15 | X15 | X15 |
| B | S2 | S2 | S2 | C2 | C2 | C2 | X8  | X8  | X8  | X16 | X16 | X16 |
| C | S3 | S3 | S3 | X1 | X1 | X1 | X9  | X9  | X9  | X17 | X17 | X17 |
| D | S4 | S4 | S4 | X2 | X2 | X2 | X10 | X10 | X10 | X18 | X18 | X18 |
| E | S5 | S5 | S5 | X3 | X3 | X3 | X11 | X11 | X11 | X19 | X19 | X19 |
| F | S6 | S6 | S6 | X4 | X4 | X4 | X12 | X12 | X12 | X20 | X20 | X20 |
| G | S7 | S7 | S7 | X5 | X5 | X5 | X13 | X13 | X13 | X21 | X21 | X21 |
| H | B  | B  | B  | X6 | X6 | X6 | X14 | X14 | X14 | X22 | X22 | X22 |

Analyte 4

|   | 1  | 2  | 3  | 4  | 5  | 6  | 7   | 8   | 9   | 10  | 11  | 12  |
|---|----|----|----|----|----|----|-----|-----|-----|-----|-----|-----|
| A | S1 | S1 | S1 | C1 | C1 | C1 | X7  | X7  | X7  | X15 | X15 | X15 |
| B | S2 | S2 | S2 | C2 | C2 | C2 | X8  | X8  | X8  | X16 | X16 | X16 |
| C | S3 | S3 | S3 | X1 | X1 | X1 | X9  | X9  | X9  | X17 | X17 | X17 |
| D | S4 | S4 | S4 | X2 | X2 | X2 | X10 | X10 | X10 | X18 | X18 | X18 |
| E | S5 | S5 | S5 | X3 | X3 | X3 | X11 | X11 | X11 | X19 | X19 | X19 |
| F | S6 | S6 | S6 | X4 | X4 | X4 | X12 | X12 | X12 | X20 | X20 | X20 |
| G | S7 | S7 | S7 | X5 | X5 | X5 | X13 | X13 | X13 | X21 | X21 | X21 |
| H | B  | B  | B  | X6 | X6 | X6 | X14 | X14 | X14 | X22 | X22 | X22 |

Incubation with 4 plex   Figure 15A

|   | 1 | 2 | 3 | 4 | 5 | 6 | 7 | 8 | 9 | 10 | 11 | 12 |
|---|---|---|---|---|---|---|---|---|---|----|----|----|
| A | Con + | | | | | | | | | | | |
| B | Con + | | | | | | | | | | | |
| C | Con - | | | | | | | | | | | |
| D | Con - | | | | | | | | | | | |
| E | X1 | | | | | | | | | | | |
| F | X1 | | | | | | | | | | | |
| G | X1 | | | | | | | | | | | |
| H | X1 | | | | | | | | | | | |

Detection   Figure 15B

|   | 1 | 2 | 3 | 4 | 5 | 6 | 7 | 8 | 9 | 10 | 11 | 12 |
|---|---|---|---|---|---|---|---|---|---|----|----|----|
| A | Con + | Con + | Con + | Con + | | | | | | | | |
| B | Con + | Con + | Con + | Con + | | | | | | | | |
| C | Con - | Con - | Con - | Con - | | | | | | | | |
| D | Con - | Con - | Con - | Con - | | | | | | | | |
| E | X1 | X1 | X1 | X1 | | | | | | | | |
| F | X1 | X1 | X1 | X1 | | | | | | | | |
| G | X1 | X1 | X1 | X1 | | | | | | | | |
| H | X1 | X1 | X1 | X1 | | | | | | | | |

Analyte 1 | Analyte 2 | Analyte 3 | Analyte 4

Figure 16A
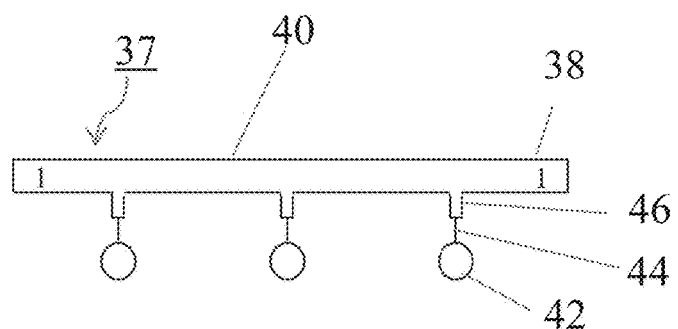
3-well strip
Figure 16C
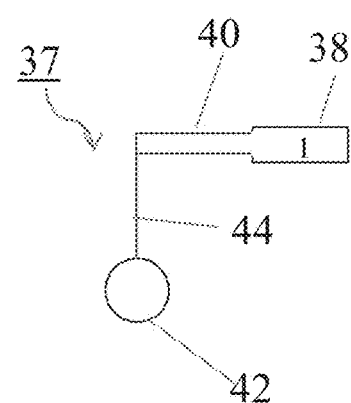
Figure 16B
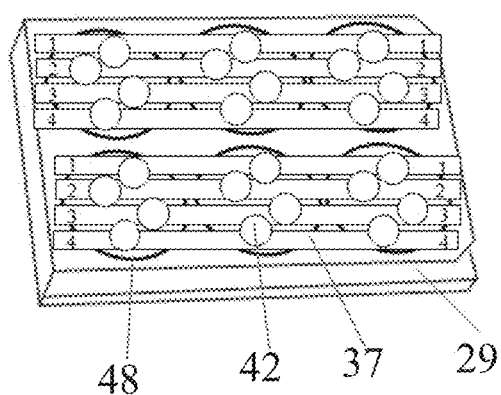
Figure 16D
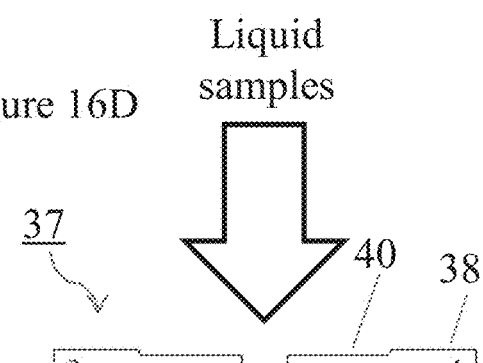
Liquid samples
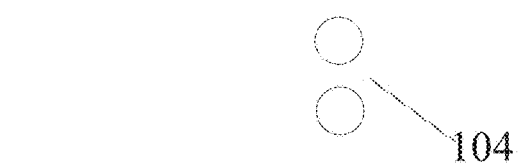

MULTIPLEX ASSAY STRIP, BEADS, DEVICE AND METHOD

CROSS REFERENCE TO RELATED APPLICATIONS

This application is entitled to priority pursuant to 35 U.S.C. § 119(e) to U.S. Provisional Patent Application No. 62/095,336, filed Dec. 22, 2014, the disclosure of which is hereby incorporated by reference herein in its entirety.

BACKGROUND OF THE INVENTION

The concept of multiplexing or "one sample application, multiple determinations" assay format had been first described by Tse Wen Chang in 1983 in his paper "Binding of cells to matrixes of distinct antibodies coated on solid surface," J. Immunol. Methods 65 (1-2): 217-23. Multiplexing has the advantage of measuring multiple analytes, such as biological molecules like protein, DNA and RNA, in one reaction array, well or test tube. It reduces the size and amounts of samples and test reagents needed for the assays and achieves the goal of generating more data with reduced time and cost.

This multiplexing concept has been widely utilized in the post-genomic era. Companies like Agilent Technologies, Inc., Illumina, Inc., Affymetrix, Inc. and Life Technologies Corporation (ProtoArray®) have produced many high density multiplex array products that can test analytes ranging from hundreds to the whole genome. Recent progress has been made by companies like Luminex Corporation, NanoString Technologies, Inc., Sequenom Inc., Meso Scale Diagnostics, LLC (MSD) and many others that focus on the medium to low density multiplex assays. Multiplexing 1 to 40 analytes seems to have satisfied most of the practical needs for life science research or clinical diagnostics.

The crucial step in multiplexing is to associate each signal to its corresponding analyte. As an array is a systematic arrangement of objects, usually in rows and columns, computer software can easily track the position and the corresponding analyte. Consequently, Agilent Technologies, Inc., Illumina, Inc., Affymetrix, Inc., Life Technologies Corporation and many other companies specialized in high density multiplex array products rely on an array system to track signals to analytes [Tse Wen Chang, supra; Schena, M.; Shalon, D.; Davis, R. W.; Brown, P. O. (1995), "Quantitative Monitoring of Gene Expression Patterns with a Complementary DNA Microarray," Science 270 (5235): 467-70]. Except MSD and others, companies focusing on the medium to low density multiplex assays like Luminex Corporation, NanoString Technologies, Inc., and Sequenom Inc. use different platforms from the array system to track analytes. These three appear to be the same in that they can multiplex in a well in suspension. However, they are quite different in how the signal is linked to its corresponding analyte. Luminex has its pride bead-based technology. Each bead or microsphere (about 5.6 microns) has a specific color code and serves as a barcode for a specific analyte. NanoString thrives on its digital molecular barcoding technology that tracks each analyte. It was invented by Dimitrov and Dunaway ["Direct multiplexed measurement of gene expression with color-coded probe pairs," *Nature Biotechnology* 26 (3): 317-25 (2008)]. Sequenom identifies each analyte strictly by its mass. This technology is built on the speed and accuracy of Matrix-Assisted Laser Desorption/Ionization Time-Of-Flight mass spectrometry (MALDI-TOF MS).

All the above multiplexing technologies have the following common aspects: They all depend on expensive and finicky equipment to detect signals and/or associate the signals to the identities of analytes. Reagents specific to each technology also need to be purchased by researchers. Basically, the essential lab equipment, such as a plate reader, in any life science or clinical laboratories cannot do the work. In addition, they are not efficient or flexible in testing a few samples or a few analytes within a day, which is usually desired in daily clinical practice. Furthermore, specially trained and dedicated technical staffs are required to operate those machines and interpret the raw data. Most of the labs either do not use multiplex assays or have to use core facilities to do the experiments. In the end, the advantages of multiplex assays, such as saving time or money, are not materialized at the end user level. Also, the current high or low density multiplex assays are so complex that it is difficult to generate reproducible data that can pass FDA regulations and be acceptable assays for clinical diagnostics.

Many companies have come up with solutions that do not require those high-tech machines. They are integrating the essential tools in all life science and clinical laboratories, such as microtiter plates, plate readers and qPCR machines. Those assays are singleplex assays measuring a few analytes on a 96-well plate or a 384-well plate. Major companies include Qiagen N.V. and Applied Biosystems/Life Technologies, Inc. Qiagen N.V. has produced many products to measure proteins or quantify nucleic acids, such as their Multi-Analyte ELISArray and RT2 Profiler PCR Array, that can work on routine lab equipment such as a qPCR machine or a plate reader. Essentially, the methods do enable the measurement of multiple analytes in one plate, and it also works well with small number of samples. However, they are singleplex, so they do not have the advantages of multiplex assays, such as reducing the size or quantity of samples or reagents and time and money. Applied Biosystems has also made many similar PCR arrays, which intrinsically have the same issues as Qiagen. Recently, Applied Biosystems did introduce an improved version of PCR arrays—the OpenArray. This platform does reduce the usage of samples and reagents and time with its 33 nl reaction volume and high throughput capacity. However, it runs into the same problems as the companies in the multiplexing arena—expensive, dedicated equipment and technical staff and is not efficient or flexible in testing a few samples or analytes and/or genes. So, these solutions do not keep the merits of multiplexing and address the issues of making multiplexing technologies readily available and simpler to use as essential lab tools.

Current target enrichment methods mainly use microspheres and/or centrifugation methods. "Protocol for the fast chromatin immunoprecipitation (CHIP) method" is a representative example of target enrichment approach [Joel D Nelson, Oleg Denisenko & Karol Bomsztyk, Nature Protocols 1, 179-185 (2006)]. Commercial companies, such as Roche's SeqCap EZ Human Exome Library v3.0 and Agilent's SureSelect, also depend on microsphere and/or bead methods to enrich targets. There has been a long-felt unsolved need for an easier alternative method for target enrichment, especially in a multiplex format, which can be further applied to target purification if purity is also desired.

In the post-genomic era, life science research and clinical applications are moving towards pathway, biomarker based studies. Biomarkers are guiding the drug development process, and they are crucial in the formation of the best treatment plans for patients or personalized medicine ["Integration and use of biomarkers in drug development, regulation and clinical practice: a US regulatory perspective," Shashi Amur et al, Biomarkers Med. (2008) 2(3), 305-31]. A validated biomarker panel for clinical research or practice and routine studies usually contains less than 10 analytes ["Multitarget stool DNA testing for colorectal-cancer screening", N Engl J Med. 2014 Apr. 3; 370 (14):1287-97]. Ideally, biomarkers can be measured via non-invasive methods, which require them to be present in peripheral body tissue and/or fluid, such as blood, urine, etc. Also, the methods to detect or measure the biomarkers need to be easy, fast, affordable, reproducible and robust ["Biomarkers on a roll", Nature Biotechnology 28, 431 (2010)]. Few of the aforementioned multiplex assays meet these criteria.

There is a great demand for a user friendly, flexible, reproducible, affordable, low density and routine multiplex assay system to capitalize on genomic information in bettering our lives. Therefore, there is a need in the art to develop simplified methods for multiplex assays and multiplex target enrichment or purification so as to make them a routine lab tool in research and clinical practice. The present invention satisfies these long-felt, unsolved needs.

BRIEF SUMMARY OF THE INVENTION

This application relates to the invention of a system including devices and methods of using them that the applicant has coined the "MobileArray™" (MA) system. Substance or chemical interaction/reaction occurs on the surface of macrospheres that are trackable. This feature enables multiplex assays to be carried out in tubes or wells. It retains the advantages of Luminex based multiplex assays but does not depend on expensive and finicky equipment. With the MobileArray™ system, a multiplex assay can be performed by anyone who can run an enzyme-linked immunosorbent assay (ELISA) using a plate reader. The MobileArray™ system can also be utilized in immunoprecipitation and target enrichment or purification in a multiplex manner. The MobileArray™ system can also be integrated in an automated procedure. This paves the road for applying multiplexing format in routine lab work, clinical diagnostics, food safety inspection, etc.

One aspect of the invention is a macro bead for use in multiplex analyte analyses, enrichment or purification comprising a bead having a surface that can accept a coating of a substance, which when subjected to a procedure may interact or react with an analyte to provide a result of analysis, enrichment or purification for the analyte, the macro bead being capable of being distinguished from like macro beads by way of unique identifiers.

Another aspect of the invention is a strip for use in multiplex analyte analyses, enrichment or purification, the strip comprising at least one macro bead attached to the strip, the macro bead having a surface that can accept a coating of a substance, which when subjected to a procedure can interact or react with an analyte to provide a result of analysis, enrichment or purification for the analyte.

Still other aspects of the invention include a subassembly and an assembly including the strips mentioned above with other components for use for convenient and efficient multiplex assays, enrichment or purification of one or more analytes.

Yet other aspects of the invention relate to methods for analyzing, purifying or enriching at least one analyte, the method comprising coating at least one macro bead by itself or at least one macro bead attached to the strip as mentioned above with the substance, subjecting the at least one coated bead with an analyte that may interact or react with the substance on the at least one bead, and analyzing the analyte subjected to the at least one coated bead to provide a result of analysis, or enriching or purifying the at least one analyte. The result of analysis may be a qualitative or quantitative analytical result. The methods preferably include the use of at least two analytes for analysis, enrichment or purification in a multiplex manner. Further, any of the methods may be integrated with any automated process for the analysis, purification or enrichment.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, the drawings show embodiments which are presently preferred. It should be understood, however, that the invention is not limited to the precise arrangements and instrumentalities shown.

In the drawings:

FIG. 5A is a top plan view of one embodiment of a plate.

FIG. 5B is a front elevation view of a plate having three wells and showing an end view of four strips in a single well in the plate.

FIG. 5C is an enlarged partial cross section of a plate.

FIG. 5D is an enlarged partial top plan view of a plate.

FIG. 14A is a map for an exemplary organization of samples in all wells of a plate during incubation steps of a 4 plex ELISA using the MobileArray™ system.

FIG. 14B is a map for an exemplary organization of samples in all wells of a plate during detection steps of a 4 plex ELISA using the MobileArray™ system.

FIG. 15A is a map for an exemplary organization of samples in one column of a plate during incubation steps of a 4 plex ELISA using the MobileArray™ system.

FIG. 15B is a map for an exemplary organization of samples in 4 columns of a plate during detection steps of a 4 plex ELISA using the MobileArray™ system.

FIGS. 16A-16D schematically illustrate various types of strips or beads of MobileArray™ systems used in exemplary embodiments for samples with large volumes in multiplex target enrichment or purification process.

DETAILED DESCRIPTION OF THE INVENTION

Unless otherwise defined, all technical and scientific terms used herein have the same meaning as commonly understood to one of ordinary skill in the art to which this invention pertains. Otherwise, certain terms used herein have the meanings as set forth in the specification.

As used herein and in the appended claims, the singular forms "a," "an," and "the" include plural references unless the context clearly dictates otherwise.

As used herein, the term "analyte" refers to a biological or chemical substance being measured, or whose presence is otherwise being determined in a sample. An analyte may be a protein, nucleic acid, bacteria, virus, cell or other molecule or particle of interest.

As used herein, the term "antibody" refers to a protein which identifies and binds, or otherwise forms an interaction with, an analyte of interest. The antibody may be a primary, secondary or capture antibody and may further be bound to an enzyme.

As used herein, the term "kit" refers to a set of reagents and devices needed to perform an assay starting from samples to final raw data, and may also include instructions for using the devices according to the MobileArray™ system.

One objective of the current invention is to simplify the multiplex assay while keeping its merits. Another objective of the current invention is to make the multiplex assay an easy procedure that can be implemented in any life science, food safety and/or clinical lab with minimal training or spending. A further objective of the current invention is to make the multiplex assay flexible so that it is as effective to run a few samples as to run many samples. Yet another objective is to utilize the current invention to simplify target enrichment and/or purification process in a singleplex or multiplex format.

The merits of the current invention will become apparent in the following description and claims.

The present invention provides a device and method to perform many laboratory assays in multiplex formats. The device, its components and system using it and them, referred to herein as the "MobileArray™" or "MA" device, components, system and method, are useful in simplifying laboratory assay protocols, preferably and specifically laboratory assays, enrichment or purification of more than one analyte, while reducing the assay time, cost and the need for expensive specialized laboratory equipment.

Figure 1A:
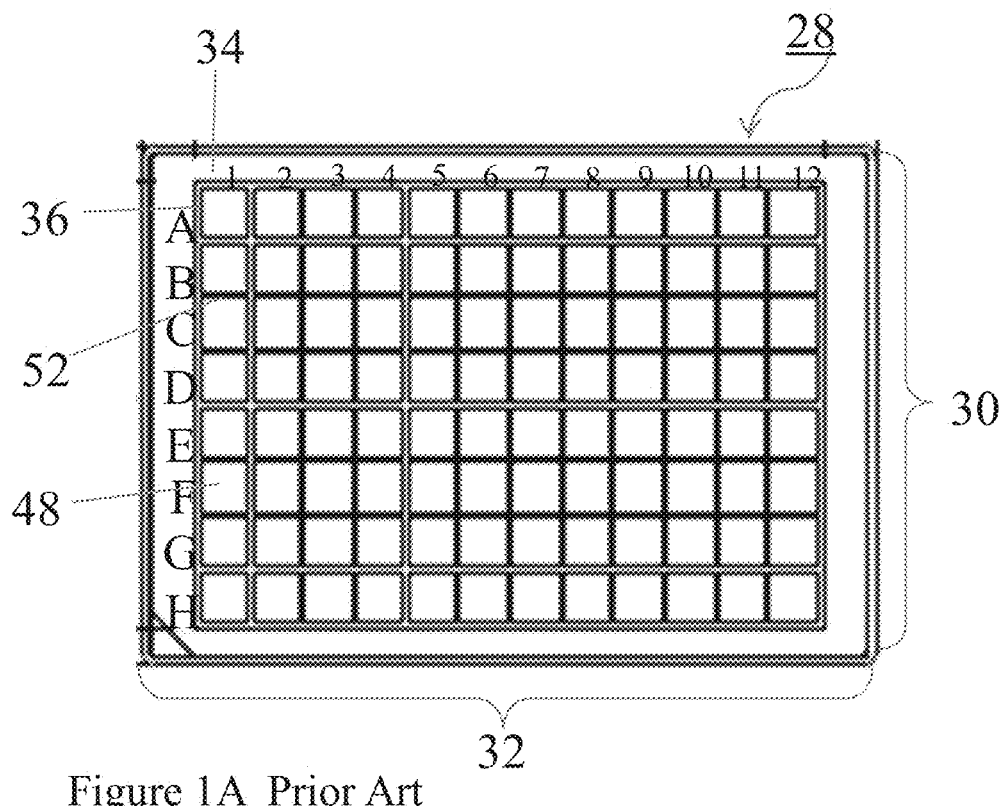
FIG. 1A is a top plan view of a standard 96-well plate with square shaped wells.
Figure 1B:
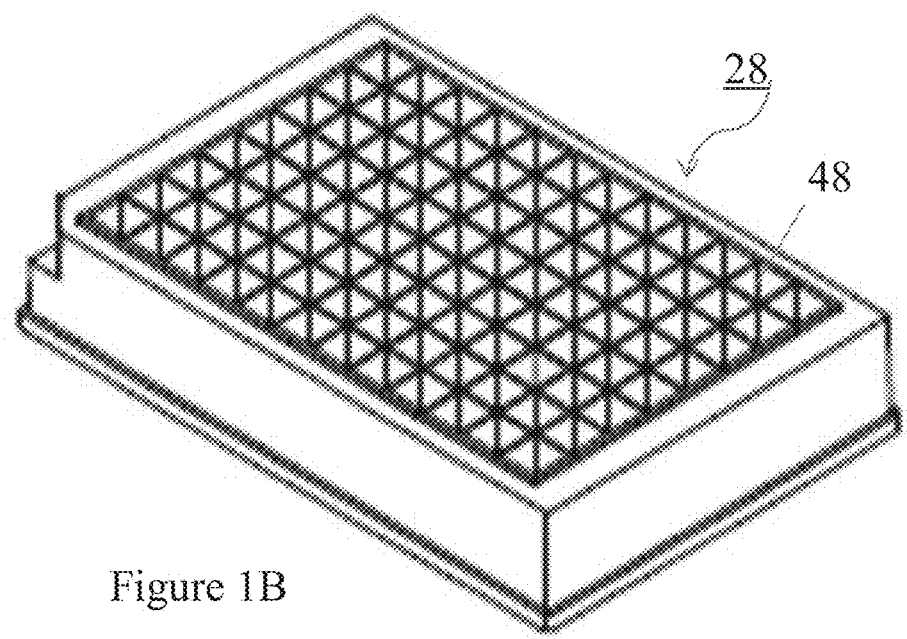
FIG. 1B is an isometric view of the standard 96-well plate of FIG. 1A.

Microtiter plates, also referred to herein as "plates," and plate readers have become essential tools in laboratories. A standard plate may have 6, 12, 24, 48, 96, 384 or more wells arranged in a 2:3 rectangular matrix format. FIG. 1A is a top plan view of a standard plate with 96 square wells. The plate 28 in FIG. 1A is arranged in an array of columns 34 and rows 36 of wells 48. One example of a standard plate with 96 wells has a width of 85.5 mm and a length of 127.8 mm, wherein the width is shown in FIG. 1A as reference numeral 30 and the length is shown as reference numeral 32.

MobileArray™ strips and other components are designed to fit current standard plates, various test tubes, or any other format system. As substance or chemical interaction/reaction occurs on the surface of macrospheres that are trackable in the MobileArray™ system, it enables the conversion of a conventional fixed array to a mobile and mixable array in liquid suspension just like the Luminex platform but without its expensive cost. Furthermore, it also enables the simplification and simultaneous enrichment or purification of multiple targets in one sample or many samples, which Luminex platform cannot. The MobileArray™ (MA) system and its component devices may comprise one or multiple of the following aspects of the invention described using 96-well plates. Modification and variation may be made to any of the following aspects so as to optimize the MA system for use with 96-well plates, or other plate or tube formats.

Figure 2:
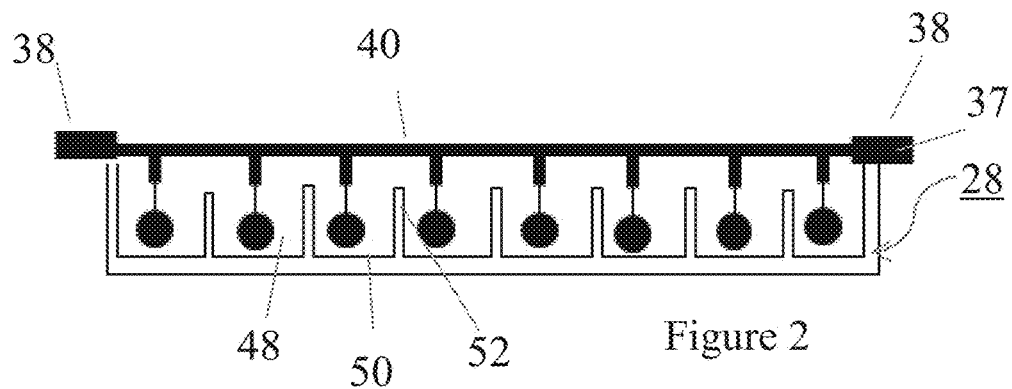
FIG. 2 is a side elevation view of a strip in plate wells from a cross section of a plate.
Figure 3A:
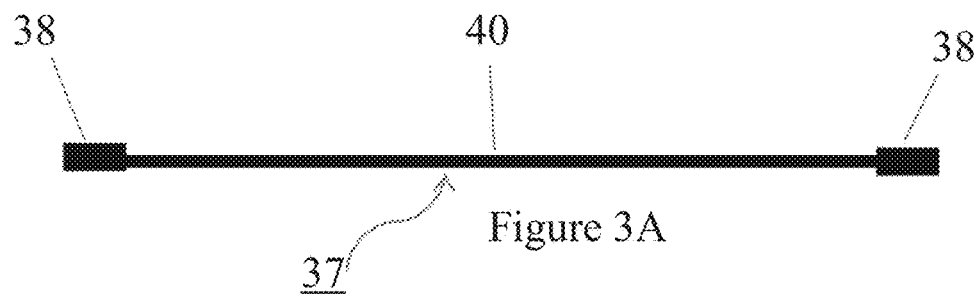
FIG. 3A is a top plan view of the strip of FIG. 2.
Figure 3B:
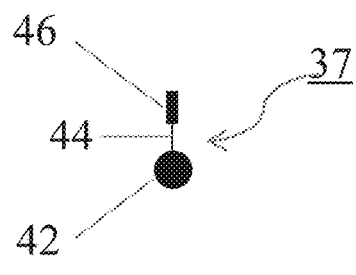
FIG. 3B is a front end elevation view of the strip of FIG. 2.
Figure 3C:
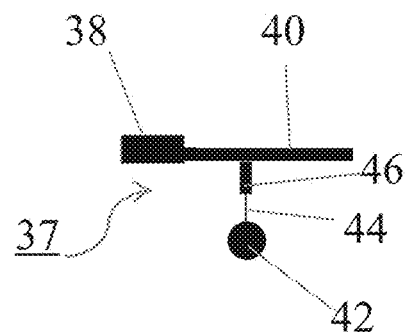
FIG. 3C is a partial side elevation view of a strip.
Figure 3D:
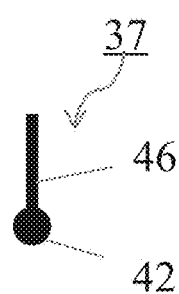
FIG. 3D is a front end view of an alternative embodiment of a strip.

One aspect of the invention is a MA strip 37 shown in FIGS. 2, 3A, 3B, 3C, 3D, 4A and 4B, also referred to herein as "strip," wherein a strip 37 comprises a bar member 40 and at least one MA macro bead 42, which is a macrosphere or bead of another shape, also referred to herein as "bead," preferably with a radius or other minimum dimension, for example length, width, height or diameter, equal to or greater than one millimeter. However, the bead may have any other suitable minimum dimension, for instance equal to or greater than 0.25 mm, 0.5 mm, 1 mm, 1.5 mm, 2 mm, etc., as shown in FIG. 3D. FIG. 2 is a side elevation view of a strip 37 in plate wells 48 from a cross section of a plate 28. A strip 37 can contain one bead 42 or many beads 42. For example, a strip can contain 1, 2, 3, 4, 5, 6, 7, or 8 beads. Alternatively, a strip can contain one or more bead per well into which the bead is intended to be inserted. In a preferred embodiment, a strip 37 contains one bead 42 for every well 48 of a compatible plate 28. One example as shown in FIG. 2 is a strip 37 containing eight beads, wherein each bead fits into one of eight wells in a column of a standard plate of 96 wells, such as the column 34 of the plate 28 shown in FIG. 1A. Beads 42 on a strip 37 may be attached directly to a bar member 40, also referred to herein as a "bar," to semi-rigid filaments 44, or to rigid rod members 46. In one embodiment, the beads 42 are attached to semi-rigid filaments 44, which are further attached to rigid rod members 46, which are attached to a bar member 40 of a strip 37. The semi-rigid filaments 44 ensure the bead 42 can mix freely and completely in a liquid sample for coating or interacting with a desired analyte. In a preferred embodiment, the beads 42 are attached directly to the rigid rod members 46, as shown in the front end view of FIG. 3D and the isometric view of FIG. 4B. The MA strip 37 enables the tracking of signals to the corresponding analytes. This mobile, mixable and trackable simple liquid array system can easily be adapted to single tubes, other plates, or other variations. Each bead 42 actually represents one dot on a fixed conventional array. The MA system enables movement and mixing of every bead that corresponds to a dot on a conventional fixed array. In other embodiments of the MA system, the beads 42 may not be attached to one or more strips 37 when tracking of the beads 42 and analytes can be achieved via any type identification to distinguish one bead from another when necessary to do so, such as by color, pattern, texture, shape, etc., or any combination thereof. The beads 42, when used alone or when attached to rod members 46 or otherwise to strips 37, or one or more of the components of a strip may be identifiable by color, pattern, texture, shape, etc., or any combination thereof, or may be made identifiable by user markings or labeling.

The materials for the bead can be polystyrene or other materials, including newly synthesized ones that exhibit excellent binding capacity and/or specificity for analytes, for example proteins, nucleic acids and other biological materials. Some examples of the materials can be those provided by Bangs Laboratories, Inc., or various Qiagen N.V. resins, or PerkinElmer AlphaLISA® bead material. The bead can also be one material in a central core, for example glass, with the outside surface of the core coated with any or multiple of the above described materials. The surface of the bead can be further modified with existing or new technologies so as to increase binding capacity and/or specificity for certain analytes. The surface of the beads can also be tissue culture treated so that the cells will grow on the beads. The surface texture can be smooth or coarse. Each bead may be any shape, but is preferably spherical, and is coated with one analyte. In a preferred embodiment, the beads on the same strip are coated with the same analyte.

FIG. 3A is a top plan view of a strip 37 comprising one bar 40 and one labeling area 38 adjacent to each end of the bar 40, but with beads not shown for ease of illustration. The labeling area 38 may be square, round, circular, oval, triangular, or any other shape, but is preferably rectangular, and will preferably allow for labeling of the strip 37. The labeling area may be an extension of the strip 37, such as an extended bar member 40. FIG. 3B is a front end elevation view of a strip comprising at least one bead 42, at least one semi-rigid filament 44, and at least one rigid rod member 46 attached to the bar 40 of the strip 37. FIG. 3C is a partial side elevation view of a strip 37 comprising one labeling area 38 at the end of the bar 40, and one bead 42 attached to one semi-rigid filament 44 that is further attached to one rigid rod member 46 attached to the bar 40 of the strip 37. FIG. 3D is a front end elevation view of a strip comprising at least one bead 42, and at least one rigid rod member 46 attached to the bar 40 of the strip 37. The bar 40, rigid rod member 46, and semi-rigid filament 44 on the strip 37 serve to hold the beads 42 and align them in positions throughout the manufacturing and testing process. The materials to make the bar 40, rigid rod member 46, and semi-rigid filament 44 is ideally inert, sturdy, and have little to no binding capacity, for example polypropylene or other available materials, but polystyrene can also be used. Preferably, the bar, rigid rod members and semi-rigid filaments are unitarily formed together such as by an injection molding process.

Figure 4A:
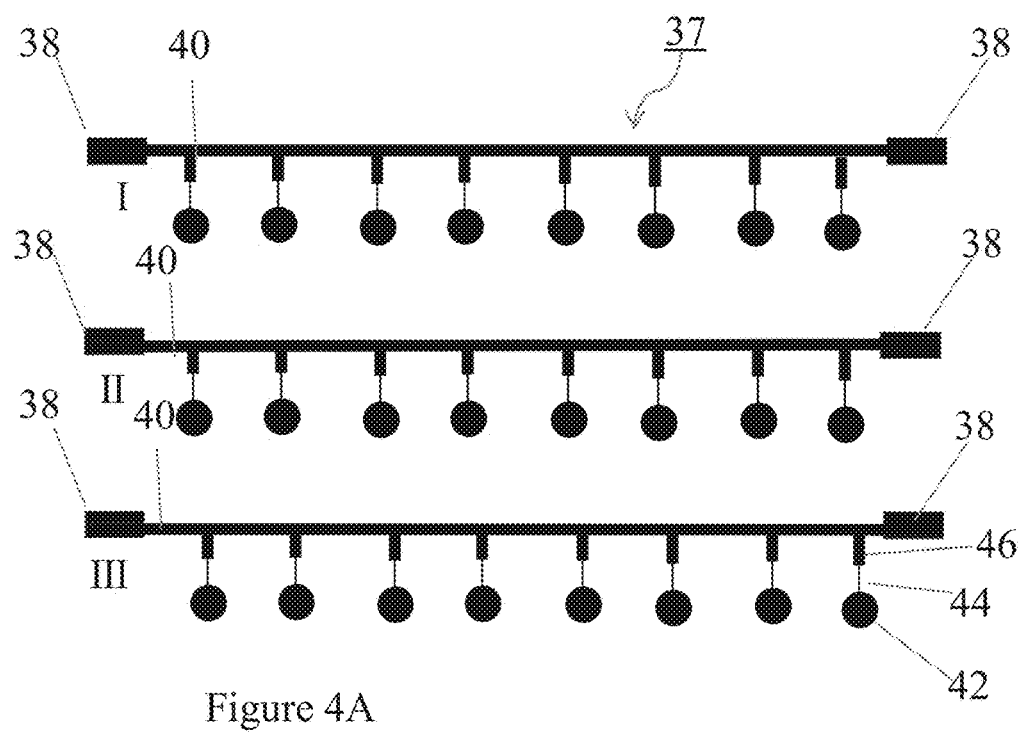
FIG. 4A is a side elevation view of several models or variations of one embodiment of a strip.
Figure 4B:
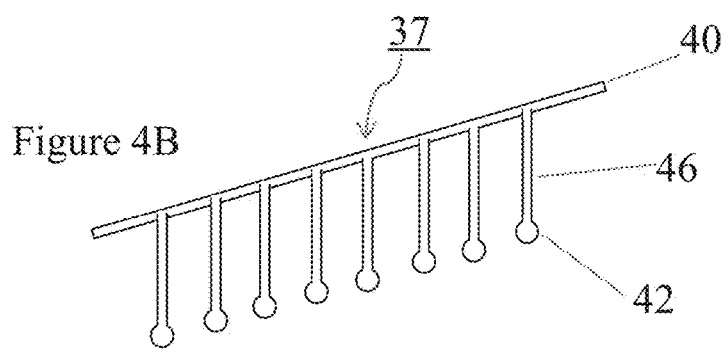
FIG. 4B is an isometric view of an alternative embodiment of a strip.

In one embodiment, the length of the bar member is 85.5 mm, or essentially equivalent to the width 30 of a plate. In a preferred embodiment, the length of the bar member is longer than the width 30 of a plate. This provides an end for gripping the strip by the protruding end of the bar member 40. The longer bar member also makes it possible to fit several of the same version or model of strips 37 in a column or a row by shifting each strip 37 slightly without the need to make different versions or models of strip 37 as shown in FIG. 4A. The height of the bar is preferably 2.0 mm, and the width of the bar is preferably 0.4 mm. The rigid rod member is preferably essentially the same width as the bar, 0.4 mm, and preferably has a length of 1.5 mm and a height of 12.5 mm. The semi-rigid filament is preferably 6.0 mm long and the bead has a preferred radius of 1.0 mm. All the dimensions can be adjusted according to the manufacturing feasibility, the plates or tubes used so as to ensure the beads sitting on the bottom of the well or very close to the bottom. The components described herein can also be produced or adapted to be utilized with commercial plates, such as those distributed by Sigma Aldrich, Thermo Fisher Scientific, VWR International, etc.

The forgoing components in a strip 37 serve to form a mobile, mixable and trackable simple array system that can test samples, enrich or purify targets in liquid suspension in a multiplex manner. A variation of the concept of converting a fixed array to a mobile and mixable array may be using visually distinguishable strips, for example by distinguishing strips, bar members or beads by color or pattern, or by beads made of or containing a small computer chip or other electronic devices. Further, some or all of the components of a strip may be loose components, may be attached, for example with adhesive, or may be molded as a unitary body. One example of some or all of the components of a strip being loose components is one or more beads placed loosely in a well or any other compartment with a liquid sample, for example a syringe body as schematically shown in FIG. 16D.

In one embodiment, three versions, models or variations of strips comprising beads are provided, wherein the beads, attached either directly to the bar or to one or more component attached to the bar, such as the semi-rigid filaments and rods discussed above, are offset in positions with respect to other similar strips so that several strips may be used together in a single well or a series of wells aligned in a column 34 or row 36 of a plate such as plate 28. For example, FIG. 4A is a side elevation view of three variations of strips according to this embodiment, model I, model II, and model III. In FIG. 4A the beads on a model II strip are shifted 2.0 mm to the right when they are aligned in parallel with a model I strip. The same is true for a model III strip when aligned in parallel with a model II strip. The purpose of the bead position variations is to make it easy to fit more than one strip and bead in each well or tube. The exemplary dimensions for the bead distributions in FIG. 4A can be modified so as to optimize fitting of more than one strip in a desired plate. The strip can be further modified to fit a column of wells in a plate, a row of wells in a plate, other plate formats, or optionally a single tube or syringe body. Three kinds of variations usually will be enough for the purpose, although other variations can also be designed. In another embodiment, the strips may be the same type, but with bar members longer than the width 30 or length 32 and may be offset manually, or not offset at all.

A second aspect of the invention is a MA microplate, also referred to herein as a "plate," wherein a MA plate comprises at least one well. A MA plate 29 is essentially a standard plate 28 as previously described, with one or more modifications to better correspond with the use of one or more MA strips 37. FIG. 5A is a top plan view of a plate 29 comprising a plurality of wells 48 arranged in an array of columns 34 and rows 36. In one embodiment, the well opening is essentially square. In another embodiment, the well 48 has a concave-shape or round bottom 50. FIGS. 5B-5D are partial enlarged views of a plate 29, as described below.

FIG. 5B is a side elevation view of a well 48 in a plate 29, wherein the middle well contains four strips 37 of alternate variations, corresponding, for example to the three models of strips 37 in parallel alignment such as Models I, II, III and I, in that order so that the beads 42 of the aligned strips 37 fit into the well 48 and can mix freely. FIG. 5C is an enlarged cross section of a portion of a plate 29. In another embodiment, one or more well walls 52 may comprise a loading groove 53 to allow for loading of a liquid sample or reagent in a well 48 by micropipette loading, for instance. For example, a loading groove 53 as shown in FIG. 5C is a slanted plane on a top portion of a well wall 52, that forms a type of miniature spout.

FIG. 5D is a partial enlarged top plan view of a plate 29 exemplifying a possible location of a loading groove 53 on a well wall 52.

In yet another embodiment, some or all of the well bottoms 50 in plate 29 may be equipped with at least one filtration hole 54 preferably in the center of well bottom 50. FIG. 5A shows this concept with respect to filtration holes 54 in the lower right portion of the plate 29. The filtration holes allow for removal of a liquid sample or reagent from a well 48. The filtration hole may be 0.5 mm in diameter and may further be covered by a membrane that prevents leaking, but permits vacuuming, for example a tightly-woven nylon membrane.

In a preferred embodiment, the plate 29 has dimensions 127.7 mm in length, 85.5 mm in width, and 20.0 mm in depth. For a 96-well plate with well walls 52 measuring 1.0 mm thick, each well can have a well opening of 8.0 mm×8.0 mm and a well depth of 19.0 mm.

Figure 12:
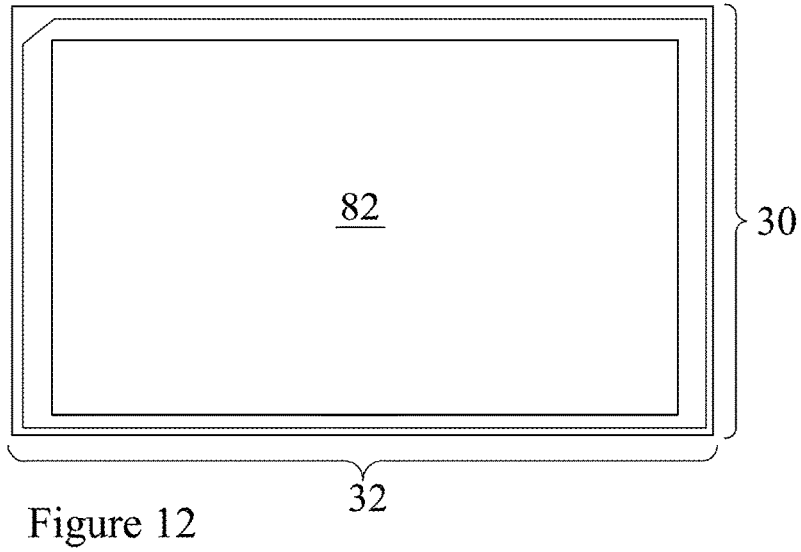
FIG. 12 is a top plan view of a tray.

A third aspect of the invention is a MA tray for strips, also referred to herein as a "tray." The tray is a modification of the standard plate 28 with only one big well. The tray may comprise one or more of any of the previously described features of the plate 29. The tray is preferably used for coating analyte on the beads, for washing the beads, or for incubating the beads in other solutions. FIG. 12 is a top plan view of a tray 82. The tray may have any desired dimensions, preferably correlated with the dimensions of the frame 62 and the divider cluster 68. Non-limiting exemplary dimensions may be 85.5 mm for an outside top width 30, 81.5 mm for an inside top width, 127.8 mm for an outside top length and 123.8 mm for an inside top length 32.

Figure 6A:
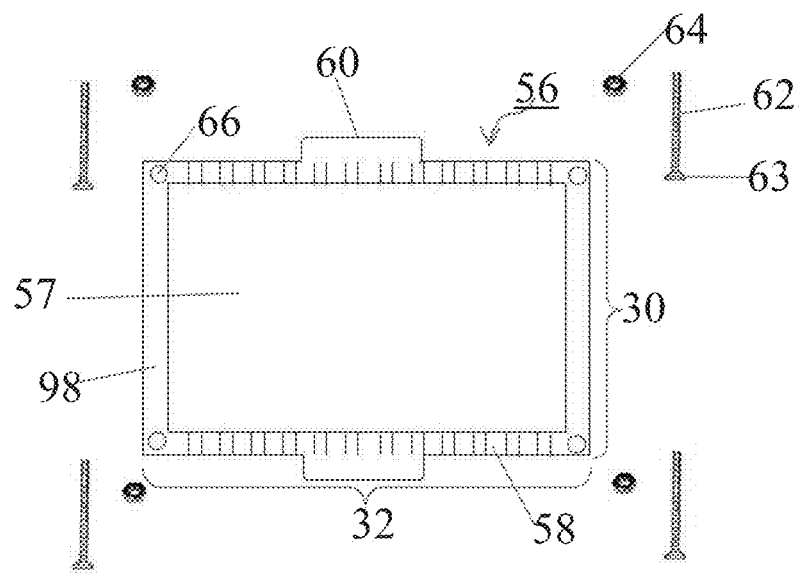
FIG. 6A is a top plan view of a frame.

A fourth aspect of the invention is a MA frame, also referred to herein as a "frame." FIG. 6A is a top plan view of a frame 56. A frame 56, optionally but not essentially, may comprise one or more handles 60 located on an outer periphery of the frame 56. The handles aid in lifting the frame, especially when multiple MA strips are on the frame, and may be square, circular, oval, triangular, but are preferably rectangular. The handles also may provide supports for banding together components of a subassembly or assembly of components, as discussed below. The frame 56 may further comprise one or more holes 66 located adjacent to any and preferably all of the four corners of the frame 56. Alternatively, in place of the holes 66, the frame 56 may comprise one or more pins 67, each located adjacent to any and preferably at all of the four corners of the frame 56, as shown in FIG. 6C. The pins 67 can be molded integrally and unitarily with the frame 56 for use in holding together a MobileArray™ assembly of the components, as discussed below. The outer dimensions of the frame 56, width 30 and length 32, are preferably essentially equivalent to the dimensions of a plate 29 or tray 82 to be utilized with the frame 56. An inner opening 57 is preferably rectangular, and large enough to ensure that no well 48 of a plate 29 to be utilized with the frame is completely covered when the frame 56 is placed over the plate.

Figure 6B:
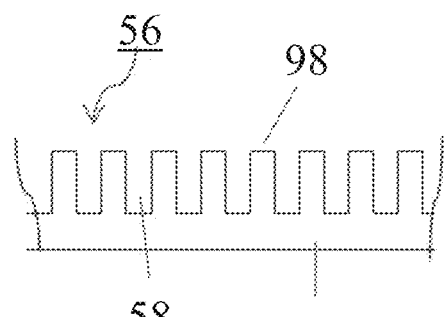
FIG. 6B is an enlarged partial front elevation view of the frame of FIG. 6A.
Figure 6C:
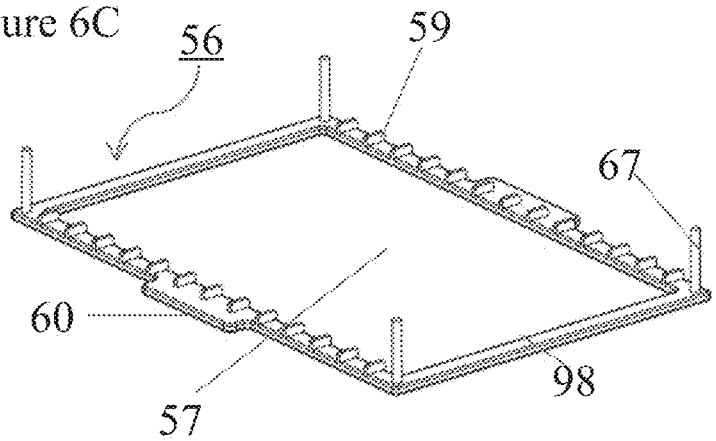
FIG. 6C is an isometric view of the frame of FIG. 6A.

FIG. 6B is an enlarged partial side elevation view of a frame 56. The frame 56 may further comprise slots 58, wherein each slot accommodates one or more bar members 40 of strips 37. The slots 58 are preferably adjacent to a top surface 98 of the frame 56 and extend towards a bottom surface 100 of a frame 56. The slots 58 preferably do not reach the bottom surface 100 of the frame 56. Alternatively, the frame 56 may comprise ridges 59, wherein each ridge may separate space on the frame 56 for one or more strips 37 to be placed, each space preferably corresponding to one column or one row. The ridges are preferably adjacent to a top surface 98 of the frame and extend upwards, but are preferably shorter than pins 67. The ridges 59 can be molded integrally and unitarily with the frame 56. In a preferred embodiment, the height of the frame is 1.5 mm, the outer dimensions of the frame are 85.5 mm and 127.7 mm, or essentially equivalent to the preferred outer dimensions of a plate 29, and the inner opening has dimensions 77.5 mm and 119.8 mm, corresponding to an inner width and length, respectively.

Figure 7A:
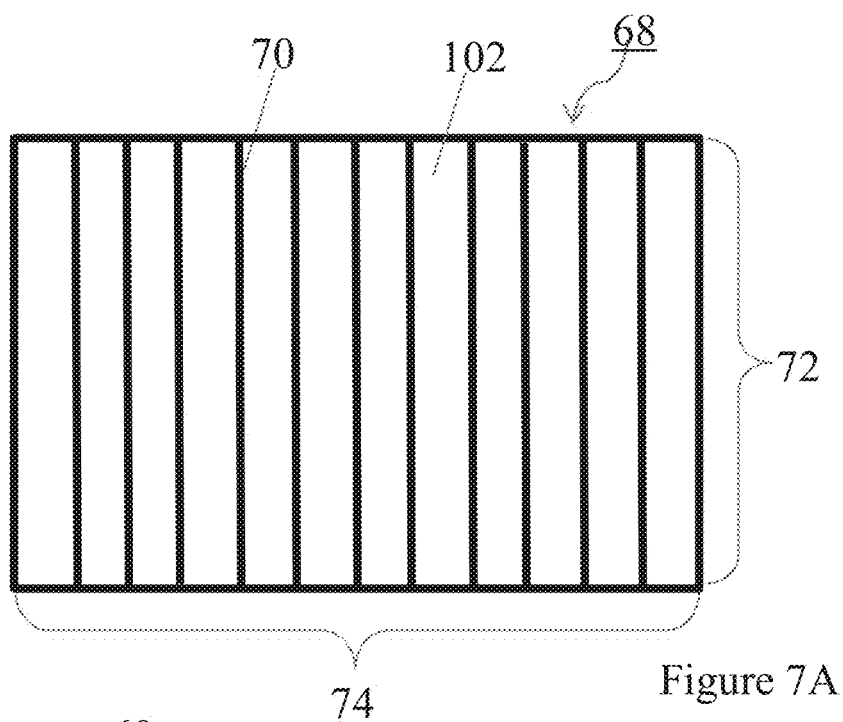
FIG. 7A is a bottom plan view of a divider cluster.

A fifth aspect of the invention is a divider cluster, wherein a divider cluster comprises at least one divider member. In a preferred embodiment, divider members are arranged parallel to each other on a bottom surface of the divider cluster and are spaced to accommodate one column or one row of wells of a plate to be utilized with the divider cluster, and to separate the strips 37 so one column or row of strips does not contact an adjacent column or row. FIGS. 7A and 7C are a bottom plan view and a bottom isometric view, respectively, of a divider cluster 68 comprising divider members 70 arranged parallel to each other and extending along the width 72 of the divider cluster 68. The divider members 70 may be molded integrally and unitarily to protrude from the bottom surface of the divider cluster 68. A divider cluster 68 is preferably rectangular in shape. In a preferred embodiment, the dimensions 72 and 74 of the divider cluster 68 are slightly smaller than the corresponding dimensions of the inner opening 57 of a frame 56 to be utilized with a divider cluster 68. In a preferred embodiment, the divider cluster has a width of 73.5 mm and a length of 109 mm.

Figure 7B:
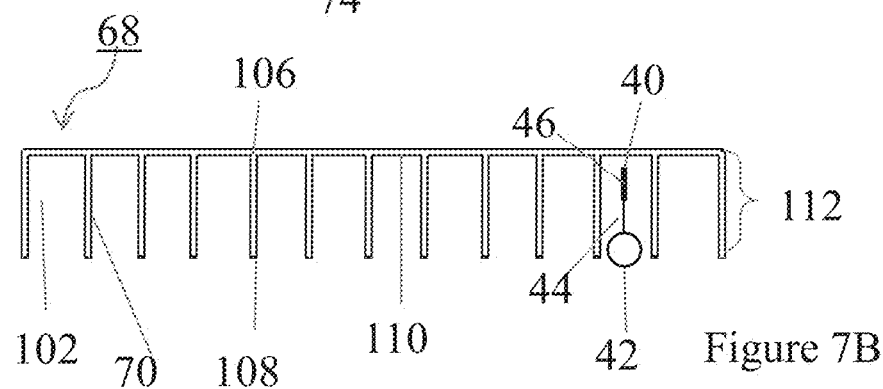
FIG. 7B is a front elevation view of the divider cluster of FIG. 7A.
Figure 7C:
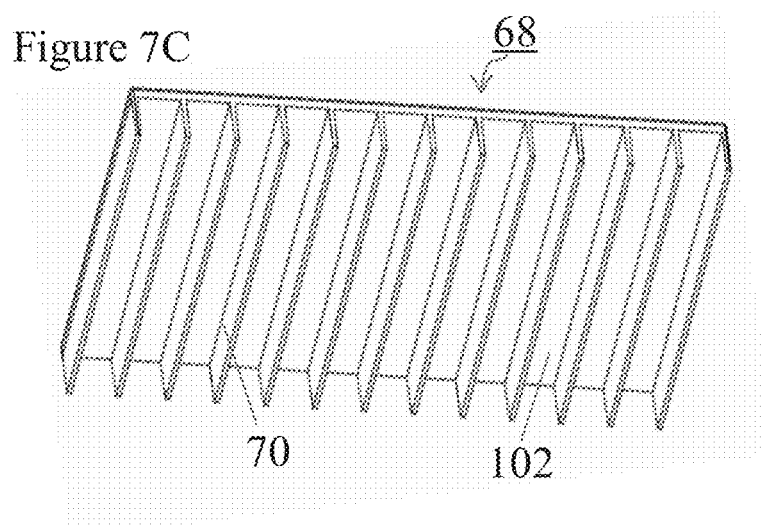
FIG. 7C is an isometric bottom view of the divider cluster of FIG. 7A.

FIG. 7B is a front elevation view of a divider cluster 68. Divider members 70 are arranged parallel to each other and extend from a bottom surface 110 of the divider cluster 68. In a preferred embodiment, the height 112 of the divider members 70 is at least enough to accommodate a strip 37, aligned parallel to the divider members 70, and adjacent to the divider cluster 68 bottom surface 110.

In a preferred embodiment, spaces 102 between divider members 70 are sufficient to accommodate one column 34 or row 36 of wells 48 of a plate 29, so that the beads 42 can extend into the wells 48 of the plate 29 to contact the solution in the wells when the divider cluster 68 in the frame 56 overlies the plate 29.

Figure 8:
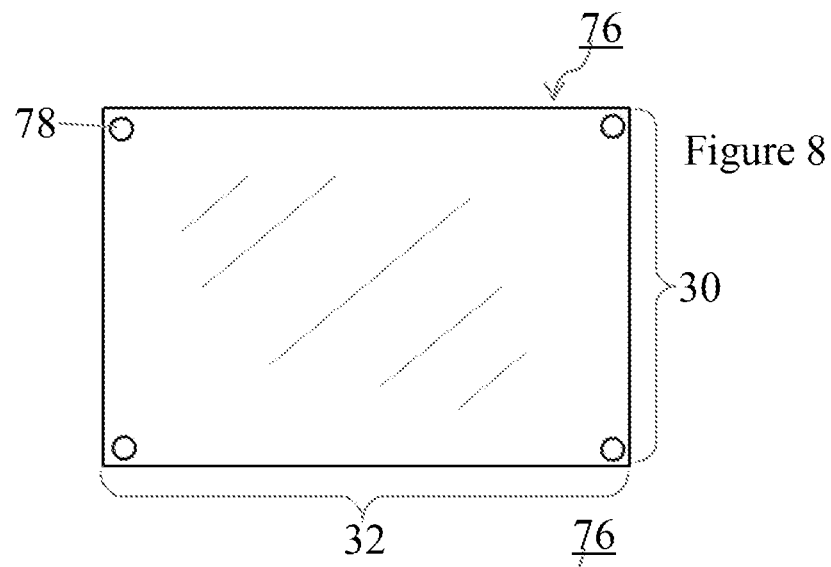
FIG. 8 is a top plan view of a top plate.

A sixth aspect of the invention is a top plate. FIG. 8 is a top plan view of a top plate 76. The top plate 76 is preferably rectangular, and the dimensions of the top plate 76, width 30 and length 32, are preferably essentially equivalent to the dimensions of a plate 29 or tray 82 to be utilized with the top plate 76, and are preferably essentially equivalent to the outer dimensions of a frame 56 to be utilized with the top plate 76. The top plate 76 may further comprise holes 78, which may or may not be threaded, and are located adjacent to any and preferably all of the outer corners of the top plate 76. The holes 78 are preferably essentially equivalent in size to the holes 66 in the frame 56, and preferably aligned with the screw holes 66 in the frame when the top plate 76 is placed adjacent to the top surface 98 of the frame. Alternatively, the holes 78 are slightly larger in size than the pins 67 on the frame 56, and aligned such that the pins 67 on the frame 56 extend through the holes 78 when the top plate 76 is placed adjacent to the top surface 98 of the frame 56.

Figure 9:
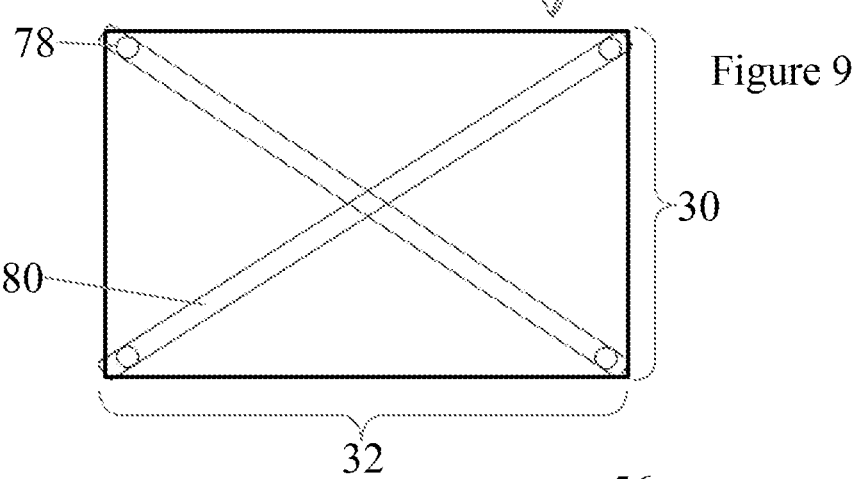
FIG. 9 is a top plan view of the top plate of FIG. 8A, wherein bearing bars are placed diagonally over the top plate.

Furthermore, the top plate may comprise one or more bearing bars or other similar structure, such as a unitarily formed peripheral frame with members internally extending to the corners and with a bottom surface in one plane that are configured to equalize the distribution of force holding the top plate 76 together with one or more of the components of the MobileArray™ assembly (described in detail below). Depending on the material used for the top plate, it may be stiff enough not to need bearing bars or another similar structure. FIG. 9 is a top plan view of the top plate 76, wherein bearing bars 80 are placed diagonally over the top plate 76 and extend from diagonally opposite corners of the top plate 76. The bearing bars or similar structure may be made of metal, such as aluminum or other rigid material, such as engineered polymeric plastic material of sufficient rigidity to equalize the distribution of force holding the top plate 76 when screws or pins are placed through contained screw holes that align with the screw holes of the top plate 76 and with the screw holes of the frame 66 to allow for screwing together one or more of the aforementioned components. Nuts 64 may be screwed onto the screws 62, and hold the bearing bars 80 against the upper surface of the top plate 76. Alternatively, the holes are aligned with pins 67 located on the frame, and the ends of the pins can be unthreaded or threaded to accommodate nuts, if desired.

A seventh aspect of the invention is a MobileArray™ assembly, also referred to herein as an "assembly" or "subassembly", wherein an assembly comprises two or more and preferably all of any of the embodiments of the aforementioned components. For example, the assembly may comprise at least one strip 37, optionally together with the plate 28 or 29, optionally with the tray 82, and frame 56, divider cluster 68, top plate 76, and optional bearing bars 80. These components may be placed over and adjacent to each other in a predetermined order. The assembly may be held together by separate screws, nuts, or the integral and unitary pins. Other assembly retention members may be used instead of or in conjunctions with the screws or pins, such as spring clamps adjacent the corners or elsewhere along the periphery of the assembly, or bands, for example rubber bands, placed over two or more components of the assembly to hold two or more components together. In a simplified embodiment, the components are held together with pins 67 located on the frame passing through holes 78 and by rubber bands extending around the assembly.

Figure 11A:
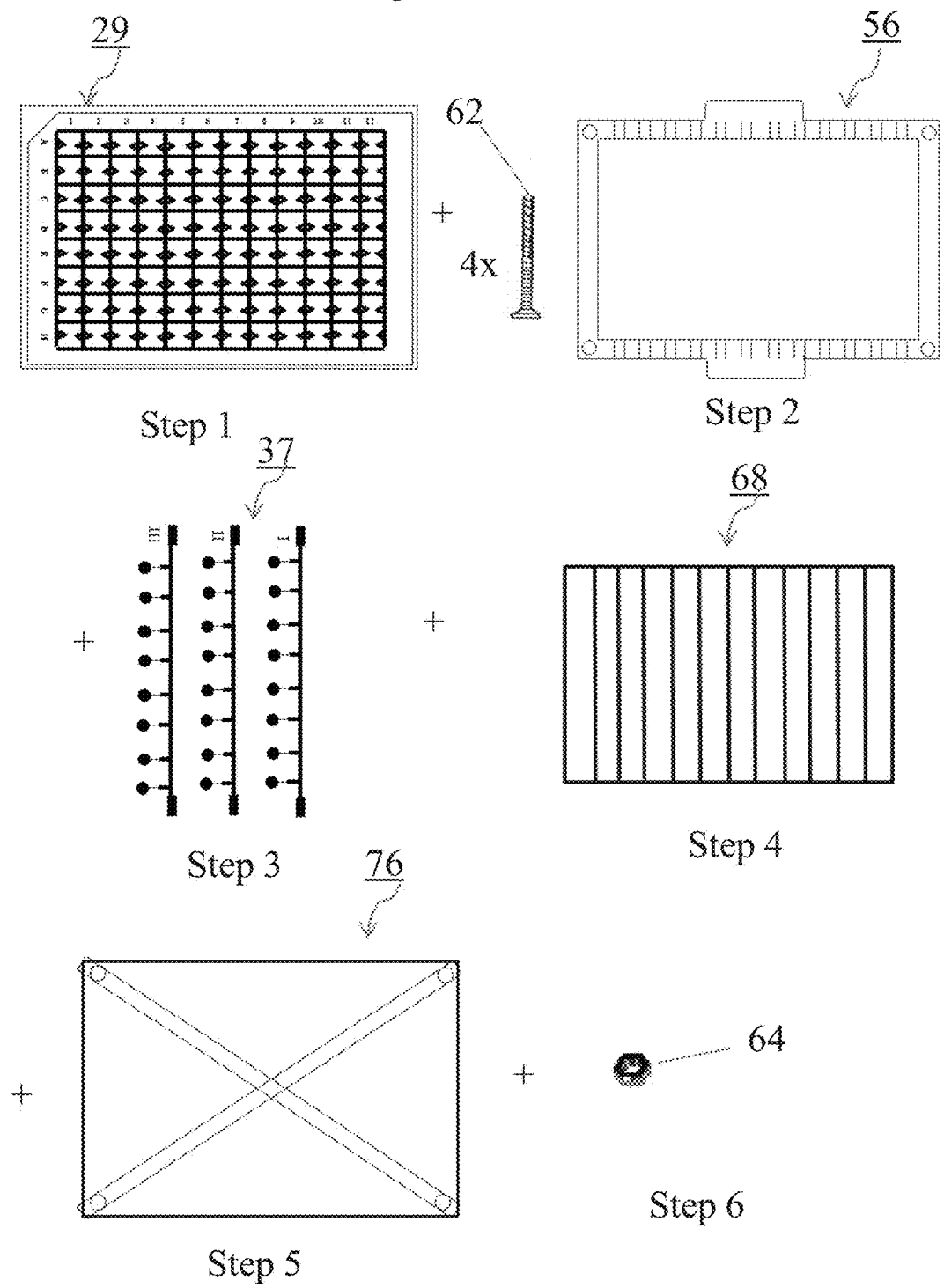
FIG. 11A is a diagram of separate components of one embodiment of a MobileArray™ assembly labeled corresponding to exemplary steps for assembling the components into the assembly.
Figure 11B:
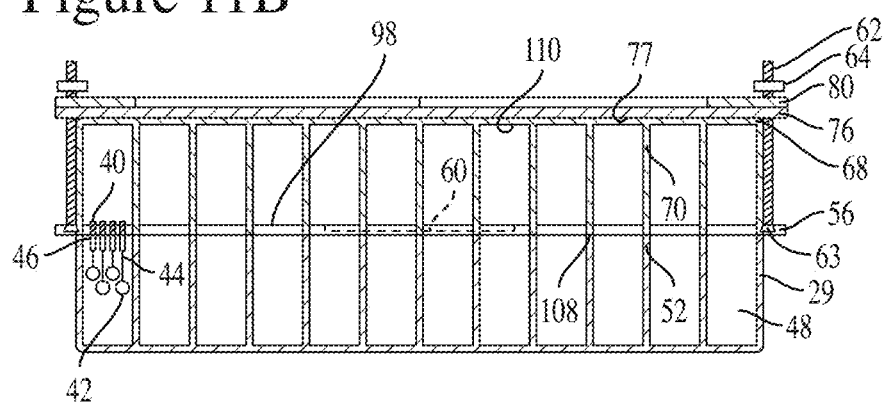
FIG. 11B is a cross-section view of one embodiment of a configured MobileArray™ assembly using the components shown in FIG. 11A.
Figure 11C:
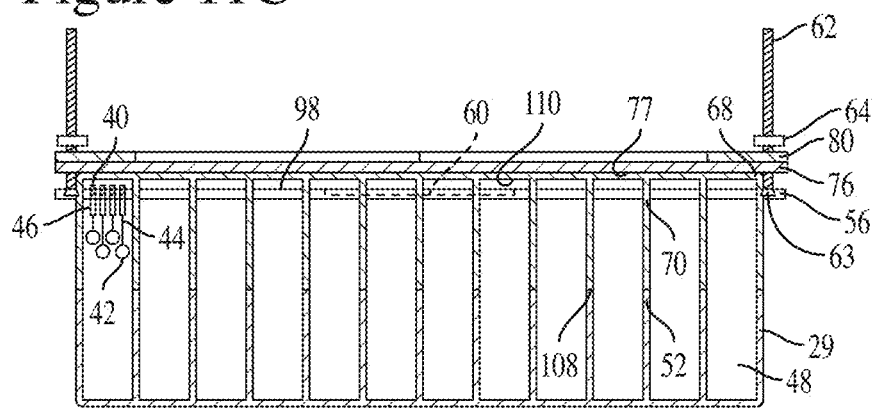
FIG. 11C is a cross-section view of another embodiment of a configured MobileArray™ assembly using the components shown in FIG. 11A.
Figure 11D:
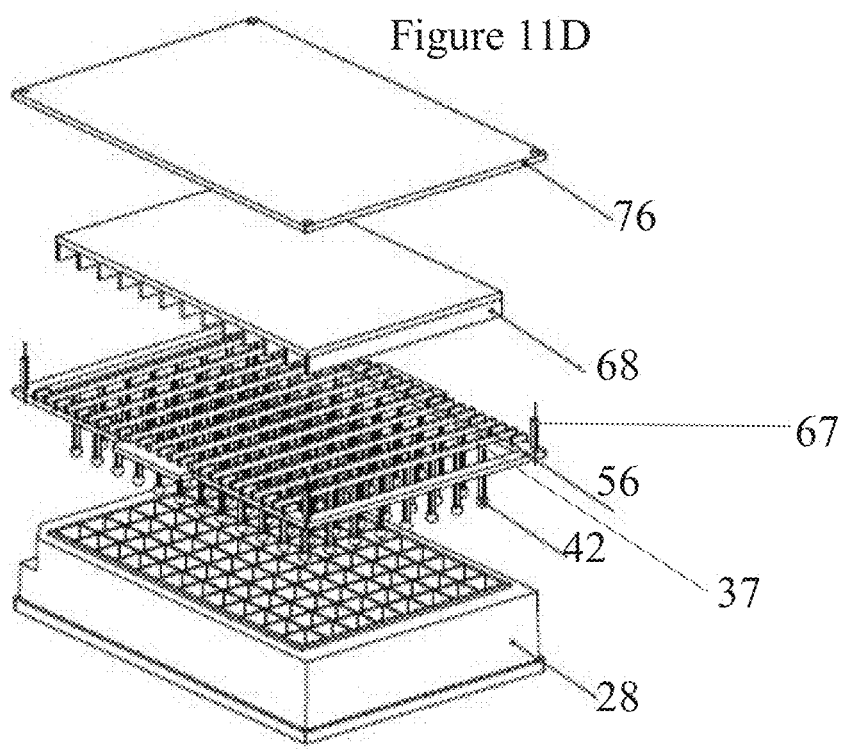
FIG. 11D is an isometric exploded view of another embodiment of a configured MobileArray™ assembly using most of the components shown in FIG. 11A.

In one embodiment, the one or more components comprising the assembly are placed adjacent to and over each other in the order as shown in FIGS. 11A and 11D, and described below:

(a) The plate 28 or preferably MA plate 29 is placed on a table or other support surface, wherein the well openings face upwards, as shown in FIG. 11A.

(b) The frame 56 is placed with the bottom surface 100 adjacent to the top of the plate 28. At least one, and preferably four screws 62 in at least one and preferably four holes 66 of the frame 56 are placed through the bottom surface 100 of the frame 56 and extend out the top surface 98 of the frame 56. The heads 63 of the screws 62 preferably are countersunk and placed into the holes 66 from the bottom of the frame. Alternatively, the screws 62 may be replaced by pins 67 that are molded as part of the frame and serve the same function as screws 62.

(c) At least one, and preferably more than one strip 37 is placed parallel to each other over the top surface 98 of the frame 56. The strip or strips 37 are accommodated in slots 58 or within ridges 59 in the frame 56. Each bead 42 of the strip 37 extends through the frame opening 57 and is aligned so as to be capable of being placed into one well 48 of the plate 28 or 29. In one embodiment there are one to ten beads 42 in each well, wherein each bead belongs to a different strip 37. In a preferred embodiment there are no more than eight beads in each well. In a particularly preferred embodiment there are no more than four beads in each well.

Figure 10:
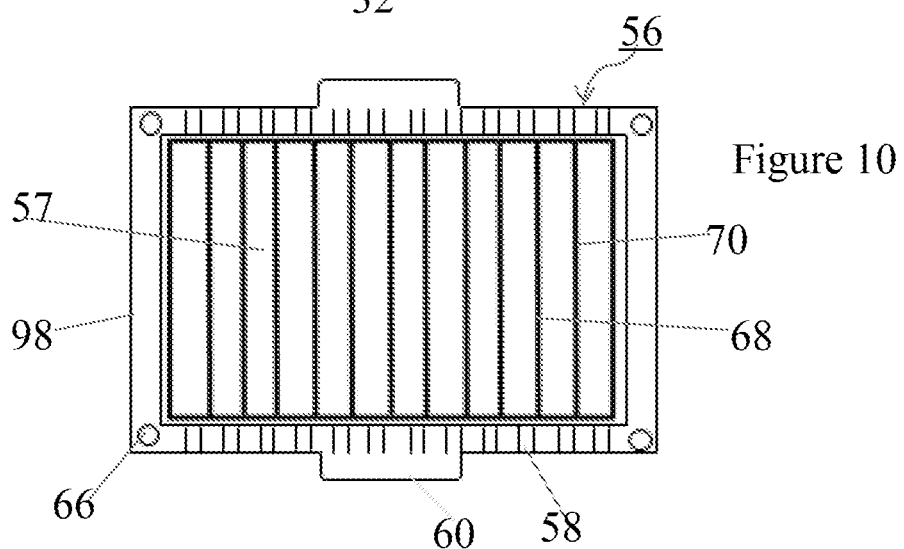
FIG. 10 is a bottom plan view of a MobileArray™ device, wherein the divider cluster is placed over the frame.

(d) The divider cluster 68 is placed within the frame opening 57 as best shown in FIG. 10, and arranged wherein the divider members 70 are parallel to the at least one strip 37, and the spaces 102 between divider members 70 accommodate all strips 37 in one column 34 or row 36 of wells, according to a preferred embodiment of the present configuration. The bottom surface 108 of the divider members 70 is adjacent to the top of the plate 29 and preferably aligned so each divider member 70 separates each column 34 or row 36 of wells, according to the present configuration.

(e) The top plate 76 is placed adjacent the top surface 106 of the divider cluster 68, wherein the top plate 76 holes 78 align with the frame 56 holes 66, and further wherein the at least one and preferably four screws 62 are placed within at least one and preferably four frame 56 screw holes 66 and are also placed within at least one and preferably four screw holes 78 of the top plate 76, extending upwards. Alternatively, the top plate holes 78 align with the frame pins 67, wherein the pins extend upwards.

(f) The bearing bars 80 may optionally be placed adjacent the top plate 76 and with their holes lined up with top plate 76 and frame 56 holes, 78 and 66, respectively, or top plate holes 78 and frame pins 67, in the same or a similar manner as the top plate 76 holes 78 are lined up with the frame 56 holes 66 and frame pins 67. In one embodiment, the bearing bars 80 or similar structure are placed diagonally over the top plate 76 and surround the some or all of the previously listed components, so as to equalize the distribution of force on the top plate and hold the components together when fastened with nuts, clamps, bands, or the like. In a preferred embodiment, the bearing bars 80 surround the frame 56, one or more strips 37, divider cluster 68 and top plate 76.

(g) In one embodiment, each of the at least one and preferably all four screws 62 are tightened with at least one and preferably all four nuts 64, holding the following components of the assembly together, to form a subassembly: the frame 56, the strips 37, the divider cluster 68, the top plate 76, and optionally, the bearing bars 80. In one embodiment, the subassembly can be held together by bands, for example rubber bands, instead of, or in addition to, nuts. In a preferred embodiment, the subassembly is held together by frame pins 67 and rubber bands.

Figure 11E:
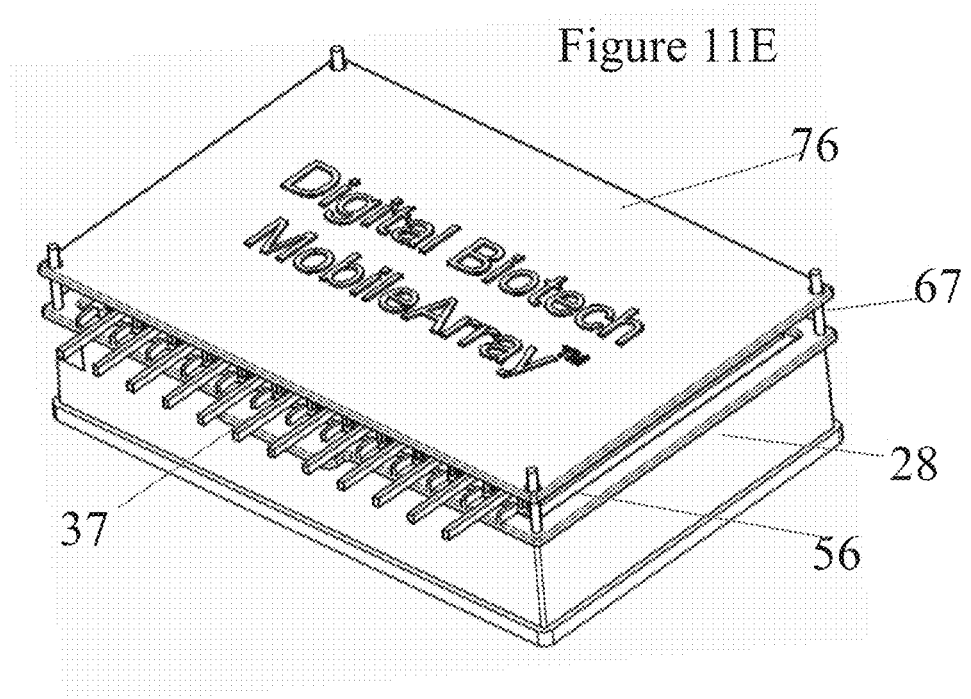
FIG. 11E is an isometric assembled view of the embodiment of a configured MobileArray™ assembly shown in FIG. 11D.

FIG. 11B is a cross section view of the assembly with the components configured as described in paragraphs (a)-(g) above, and further wherein four strips 37 are placed with beads 42 extending below the bottom surface 108 of the divider members 70 so that they may be within any solution contained in one well 48. The bottom surface 108 of the divider members 70 is shown as being adjacent to the top surface of the plate 29. FIG. 11C is a cross section view of an alternate configuration of the assembly, wherein the nuts 64 are tightened further upon the screws 62 such that the top surface 98 of the frame 56 approaches the bottom surface 77 of the top plate 76. However, in the configuration shown in FIG. 11C, by tightening the nuts on the screws, the strips 37 are held in the slots 58 or within ridges of the frame 56 against the bottom surface 110 of the divider cluster 68, and the subassembly retains the strips 37 and beads 42 in place between the divider members 70. In this way, the subassembly may be lifted as a unit off of the top of the plate 29 and moved for further processing of the beads 42 in another solution in the well of the tray 82 or in wells 48 of other plates 28 or 29. FIG. 11D is an isometric exploded view of an alternate configuration of the assembly, wherein frame 56 comprises pins 67 located adjacent to all four corners of the frame. FIG. 11E is an isometric assembled view of an alternate configuration of the assembly, wherein frame pins 67 extend upward through top plate holes 78.

Figure 13:
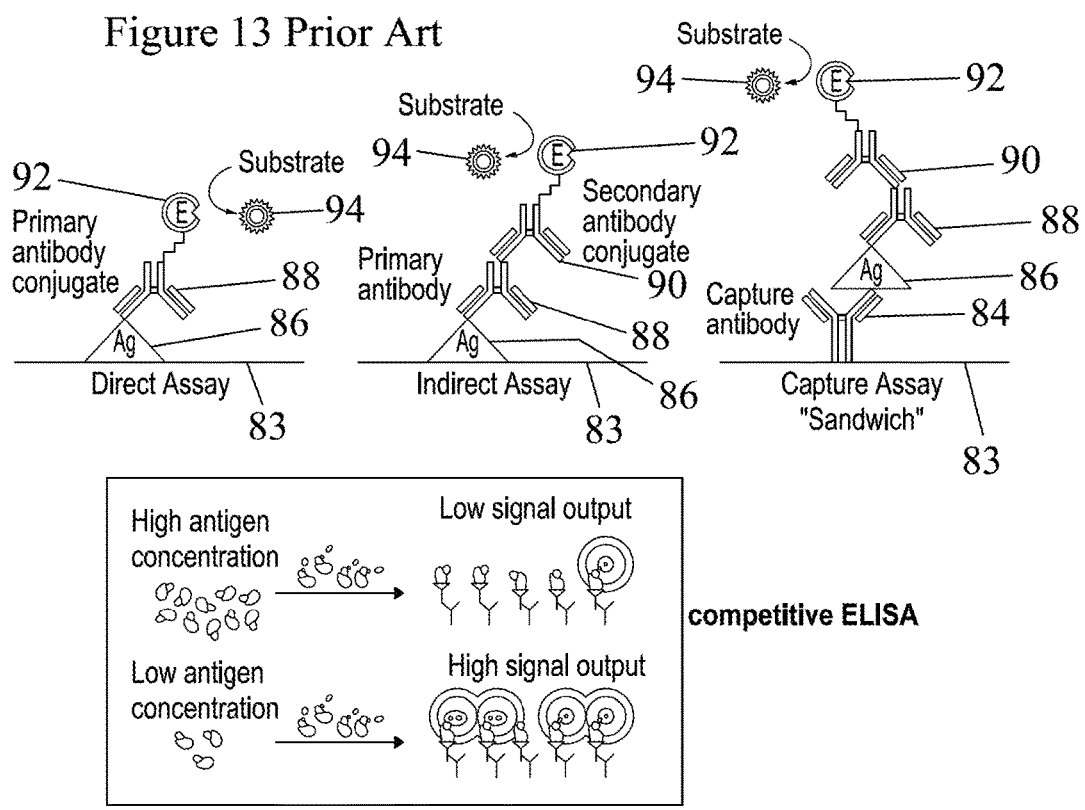
FIG. 13 is a schematic diagram of common types of ELISA Assays.

An eighth aspect of the invention is a method to perform a multiplex ELISA on the surface of beads that may be and preferably are on the strips 37. Briefly, an ELISA is a wet-lab test that uses one or more antibodies to recognize a substance. Three examples of an ELISA are shown in FIG. 13. In the assay, an analyte of interest 86 is immobilized by direct adsorption to a surface, for example well walls of a plate or a surface of a bead 42. The analyte of interest 86 may be immobilized by first attaching a capture antibody 84 to the surface, that specifically recognizes and binds the analyte of interest 86. Detection of the analyte can then be performed using an enzyme-conjugated primary antibody 88 (direct detection) or a matched set of unlabeled primary and conjugated secondary antibodies 90 (indirect detection). Following addition of an enzymatic substrate 94, the enzyme 92 catalyzes a chemical reaction and produces a visible signal, which may be, for example a visible color change (for qualitative ELISA) or a visible change read at a specific wavelength via a spectrophotometer or ELISA plate reader (quantitative ELISA). Via the visible signal, a concentration of the analyte of interest 86 in the sample may be determined. If no visible signal is produced, the sample did not contain the analyte of interest.

The method to perform a multiplex ELISA according to the present invention may be used to perform a capture multiplex ELISA, otherwise known as "sandwich" ELISA. In a capture ELISA, a capture antibody 84 is bound to a surface, for example the surface of a bead 42. The capture antibody 84 recognizes and binds an analyte of interest 86, following contact with a sample to be tested. The analyte may further be bound to a primary antibody 88 as in direct ELISA, or further to a secondary antibody 90 as in indirect ELISA.

A multiplex ELISA can also be performed in the form of a competitive ELISA using the MA system of the present invention. This is common when the analyte is small and has only one epitope, or antibody binding site. One variation of this method consists of labeling purified analyte instead of the antibody. Unlabeled analyte from samples and the labeled analyte compete for binding to the capture antibody. A decrease in signal from purified analyte indicates the presence of the analyte in samples when compared to assay wells with labeled analyte alone.

The method to perform a multiplex ELISA using the MA system of the present invention comprises contacting the sample to be tested with multiple beads 42, wherein each bead on different strip 37 is coated with a different capture antibody. Each bead coated with a different capture antibody immobilizes a unique analyte of interest from the sample. The signal from each bead 42 is associated with the specific analyte according to the matrix system of plates and labeling of strip 37. Further, each bead 42 or strip 37 may be visibly distinguishable, for example by color or pattern.

FIGS. 14A and 14B show a typical multiplex ELISA map for a quantitative test. Standards and samples are typically tested in triplicates. FIG. 14A shows the map for incubation steps. FIG. 14B shows the map for the detection step. For a 4 plex assay (detection of 4 different analytes), strips are distributed into 4 separate standard 96-well plates for final signal measuring using a plate reader.

FIGS. 15A and 15B show a multiplex ELISA map for a qualitative test of one clinical sample. Positive control (Con+) and negative control (Con−) are typically tested in duplicates, and one sample is tested in quadruplet. FIG. 15A shows the map for incubation steps. FIG. 15B shows the map for detection step. For a 4 plex assay (detection of 4 different analytes), strips from one column are distributed into 4 separate columns in a standard 96-well plate for final signal measuring using a plate reader.

The use of the MA device in accordance with the methods of the invention will now be described with reference to the following examples. It should be understood, however, that the invention is not limited to the precise parameters and embodiments shown below.

Example 1—Coating of Analytes on the Beads in Large Quantity

When large batch of beads 42 on the strips 37 coated with a designated antibody or analyte are needed, they can be produced in the following process. A MobileArray™ device assembly is assembled as previously described and according to FIGS. 11A-11E. The screws 62 are placed in the screw holes 66 of the frame, with the tips of the screws face up. Multiple strips 37 of differing models as shown in FIG. 4A, or strips 37, preferably with an extra-long bar member 40 extending beyond the width of a well plate 29 for easy handling, aligned in order, each with 8 beads, are aligned on a frame 56, which are placed over a 96-well plate 29 having twelve columns 34 and eight rows 36, so that one bead from each strip falls into each well of the first column 34 of the 96 well plate 29. The second through twelfth columns 34 are filled in the same way. The removable divider cluster 68 is placed over the frame 56 so that it fits in the inner opening 57 of the frame with the divider members 70 parallel to the strips 37. The top plate 76 is put on and the assembly is fastened with the bearing bars 80 on the top plate. The nuts 64 are tightened only to the extent to allow the beads 42 to be in the wells 48 of the plate 29. To remove the assembled strips out of the plate wells, the frame 56 is lifted by the handles 60 all the way until the bars of the strips reach the bottom surface 110 of the divider cluster 68. The nuts 64 are further tightened to retain the strips 37 against the bottom surface 110 of the divider cluster. The divider members 70 of the divider cluster 68 separate the strips from each column. This will prevent collapsing of the assembly and keep all the strips in order, so that the subassembly of the frame 56 to the bearing bars 80 can be moved as a unit without disturbing the positions of the strips 37 or the beads 42 on the strips.

Next, the whole MA subassembly can be placed upon the tray 82 with the single well as shown in FIG. 12. The tray is filled with a sample containing a specific antibody or analyte of interest at the optimal concentration in the optimal buffer corresponding to the specific analyte. The amount of the solution used should submerge all the beads 42. The whole assembly can be wrapped and incubated at 4° C. overnight (ON) or at room temperature (RT) depending on the specific antibody or analyte. Basically, if the strips are used for multiplex ELISA, conditions established for a specific analyte ELISA can be used for capture antibody coating, washing, blocking and processing of the corresponding strips. The coating process is carried out in the tray after the subassembly is put together. After coating and washing, the pre-coated strips can be sealed, such as in an aluminum vacuum packet, with one or more strips in each packet for long term storage. Large quantity of strips 37 with other designated analyte can be prepared in the same way as above. These sealed strips can be assembled in multiplex assay kits.

Example 2—Coating of Analytes on the Beads in Small Quantity

When small batch of beads 42 on the strips 37 coated with a designated antibody or analyte are needed, they can be produced in the following process. Strips can be assembled in the same way as described in Example 1 above. This time, the assembly need not be removed out of the plate. Before putting on the divider cluster, a sample containing a specific antibody or analyte of interest at the optimal concentration in the optimal buffer corresponding to the specific antibody or analyte can be added to one or two columns of wells in the plate 29, depending on how many analytes of interest will be tested. For example, strips 37 in columns 1 to 3 are coated with antibody or analyte 1, columns 4 to 6 for antibody or analyte 2, columns 7 to 9 for antibody or analyte 3, and columns 10 to 12 for antibody or analyte 4. Solution can be added through the loading grooves 53 using a multichannel pipette. The amount of solution used should submerge all the beads. This way, several small quantities of strips can be coated with different antibody or analytes using one plate. After all the corresponding solutions are added, the removable divider cluster is placed over the plate, wherein divider members are parallel to the strips. The top plate is put on and the subassembly is fastened with the bearing bars and nuts. The whole subassembly can be wrapped and incubated according to the optimal conditions for the corresponding antibody or analytes.

Basically, if the strips are used for multiplex ELISA, conditions established for a specific analyte ELISA can be used for capture antibody coating, washing, blocking and processing of the corresponding strips. After coating and washing, the pre-coated strips can be sealed, for example in aluminum vacuum packets with one or more strips in each packet for long term storage. These sealed strips can be assembled in multiplex assay kits.

Example 3—A Pre-Assembled MobileArray™ Multiplex ELISA Assembly in 96-Well Format Manufacturers can make a strip assembly in 96-well format that measures 4 protein analytes (4 plex). Protein 1 capture antibody is coated on model I strips, protein 2 capture antibody on model II strips, protein 3 capture antibody on model III strips and protein 4 capture antibody on alternate model I strips (FIG. 4A). Manufacturers can include a frame fitting 4 strips in each column. As a result, there will be 4 strips I, II, III, I that correspond to each four different analytes of interest in one column 34. Columns 2 to 12 will be filled in the same way as for column 1. The strips will be secured in the MobileArray™ assembly (FIG. 11). The whole assembly can be vacuum packed and sealed, for instance in an aluminum package for long term storage. The storage conditions should be very similar to the current conventional singleplex ELISA plates. This sealed assembly package can be used in building a complete MobileArray™ multiplex ELISA kit including other reagents.

Example 4—Customized MobileArray™ Multiplex ELISA Assembly in 96-Well Format

The customer can order beads coated with capture antibody for one or more specific analytes of interest from the manufacturers' web site. Manufacturers can assemble those individually wrapped pre-coated strips containing the beads corresponding to the analytes of interest. If the customer requests the strips to be pre-assembled in a plate, manufacturers can process the beads using the same procedures as described above in Examples 1-3. If the customer prefers to assemble the strips comprising pre-coated beads itself, manufacturers can send the customer the sealed strips comprising pre-coated beads, the plate, any further components of the assembly, and instructions. The sealed assembly or components for the assembly can be used in building a complete MobileArray™ multiplex ELISA kit in 96-well format.

Example 5—A Complete MobileArray™ Multiplex ELISA Kit in 96-Well Format

To produce a complete MobileArray™ multiplex ELISA kit in 96-well format, manufacturers can combine ELISA strips and any other components of the assembly in a 96-well format that detects several analytes for each sample with other downstream reagents. Downstream reagents may include but are not limited to two controls, standards, wash buffer, diluent, horseradish peroxidase (HRP) conjugated detection antibodies corresponding to the analytes, chromogenic substrates such as 3,3',5,5'-tetramethylbenzidine (TMB), buffers for samples. Other HRP substrates can also be used in the assays. A brochure describing in detail kit components, assay principle and assay procedure preferably is also included in the kit.

Example 6—An Experiment Using a Complete Pre-Assembled MobileArray™ 4 Plex Multiplex ELISA Kit in 96-Well Format To run a 4 plex MobileArray™ multiplex ELISA using a complete kit assembled in 96-well format, an assay can be set up according to FIGS. 14A-14B. In this example, 4 protein analytes, labeled 1-4, will be measured in triplicate. Columns 1, 2 and 3 are used for 7-points standards (S1-S7) and blank control (B). Columns 4 to 12 are used for control 1 (C1), control 2 (C2) and unknown samples 1 to 22 (X1 to X22). The MA kit assembly is assembled as in FIGS. 11A and B, so the top plate and divider cluster are removed before adding samples. Standards can be made using diluent and pipetted into the corresponding wells via the loading grooves on the 96-well plate. Blanks contain only diluents.

C1, C2 and samples can be diluted in diluents first and pipetted into the corresponding wells. The reaction volume can be 200 µl or enough to submerge all the beads. The divider cluster and top plate will be put back on the assembly and secured with bearing bars and nuts. The whole subassembly can be wrapped, for example in aluminum or plastic wrap, and incubated on a plate shaker for 2 hours at RT.

After the standards and samples are incubated, the whole subassembly (from frame to top plate and bearing bars) is taken out of the plate. This is done by lifting the frame by the handles all the way until the bars of the strips reach the bottom surface of the divider cluster. The nuts on the screws will be readjusted so as to further tighten the subassembly, as shown in FIG. 11C. Now, the divider members from the divider cluster separate strips from each column. This will prevent collapsing of the assembly and keep all the strips in order. The subassembly is placed over a tray containing wash buffer, so that beads are fully submerged in the wash buffer. The subassembly is moved up and down a few times in the buffer and transferred to another tray containing fresh buffer. This step is repeated multiple times before transferring into the tray containing detection antibodies in its corresponding buffer. The whole subassembly is wrapped and incubated on a plate shaker for 1 hour at RT.

After incubation with detection antibodies, the whole subassembly is taken out of the tray and submerged in the fresh wash buffer in a new tray. The subassembly is moved up and down a few times in the buffer and transferred to another tray containing fresh buffer. This step is repeated 3 times in wash buffer, and one time in buffer for substrate TMB. While the beads are still submerged in the buffer, the whole subassembly is disassembled by removing the nuts, bearing bars, top plate, and divider cluster. Now, all the strips are free to be removed. Since it is a 4 Plex assay, 4 regular 96-well plates, such as Costar ELISA plates, are lined up on a bench. Each well will contain 50 µl of the buffer for substrate TMB.

Each strip is removed out of the tray from the first column to the last column without skipping order, and placed in the corresponding column of a plate labeled with the analyte of interest. Plate 1 is for protein 1, plate 2 for protein 2, plate 3 for protein 3, and plate 4 for protein 4. Each bead is sitting in each well. When all the strips have been distributed to the plate in the correct columns, 50 µl of the 2× substrate TMB is added into each well using a multichannel pipette one plate at a time. The plates are incubated at RT for 5 to 30 minutes. The reaction is stopped by removing strips out of each plate. The blue color of TMB is measured at a wavelength of 620 nm-650 nm. In this case, 4 plates are measured and data are collected.

Example 7—An Experiment Using a Complete Non-Assembled MobileArray™ 4 Plex Multiplex ELISA Kit in 96-Well Format In this exemplary experiment, there is only one sample, such as a patient throat swab sample. The goal is to test for the presence or absence of 4 types of bacteria in the throat. To run this experiment, the whole 96 well plate is not needed. The test can be done in one column. Samples are arranged as seen in FIGS. 15A-15B for the incubation and detection steps. Four strips corresponding to the specific bacteria, i.e. coated with capture antibody that binds to the specific bacteria of interest, are fit into column 1 with or without a frame. Positive control (Con+), negative control (Con−) and quadruplet throat swab samples are added in the wells in the presence of the appropriate buffer. The reaction volume can be 200 µl or enough to submerge all the beads. There is no need to use further components of the subassembly or assembly, as there is only one column of strips. The 4 strips and the plate can be wrapped, for instance in aluminum or plastic wrap, and incubated on a plate shaker for 2 hours at RT.

After the incubation, the 4 strips are washed 3 times in wash buffer, and one time in buffer for detecting antibodies using a tray or one column of the plate. The 4 strips are transferred back into the column of the plate that contains detection antibodies in their corresponding buffer. The 4 strips in the plate can be wrapped, as in aluminum or plastic wrap, and incubated on a plate shaker for 1 hour at RT.

After the incubation, the 4 strips are washed 3 times in wash buffer, and one time in buffer for substrate TMB using a tray or one column of the plate. Afterwards, the 4 strips are transferred into one Costar ELISA plate for detection. Each well will contain 50 µl of the buffer for substrate TMB. Each column will now contain one strip, so that columns 1-4 of the plate contain strips. Column 1 is the strip for detecting bacterium type 1 and so on. When all the strips have been distributed to the correct columns, 50 µl of the 2× substrate TMB are added into each well using a multichannel pipette one column at a time. The plate is incubated at RT for 5 to 30 minutes. The reaction is stopped by removing strips out of each plate. The blue color of TMB is measured at a wavelength of 620 nm-650 nm. In this case, 4 columns in one plate are measured and data are collected. The remaining strips in the kit can be used for other studies.

Example 8—An Experiment Using Pre-Coated MA Strips for Multiplex Target Enrichment or Purification in Plates For example, to detect 4 kinds of bacteria in 6 food samples, incubate each sample with 4 beads that each derives from one pre-coated 3-bead strip in a 6-well plate to enrich bacteria first before running PCR reactions or other detection assays (see FIGS. 16 A and 16B). In another example, there are six samples and each has about 5 ml in volume. A researcher is interested in purifying 4 different proteins from each sample. The pre-coated 3-bead strips in a 6-well plate format are well-suited for this task. After the enrichment step as described above, extra washing steps are needed in order to purify proteins. The target to be enriched or purified can also be nucleic acids, or other analytes of interest.

Example 9—An Experiment Using Pre-Coated MA Strips for Multiplex Target Enrichment or Purification in Syringe Body In another example, the liquid food or water samples can be in a large volume with very low concentration of bacteria. Pre-coated single bead strips 37, or loose beads 42, can be placed in a syringe body. The food or water sample can be dripped through the syringe body by gravity (see FIGS. 16C and 16D) so as to enrich the bacteria for further study. Alternately, a researcher may need to purify 4 different proteins from 500 ml of cell culture supernatant. Instead of dividing the sample into 4×125 ml to go through the singleplex purification procedures, one can use pre-coated single bead strips 37, or loose beads 42 and a syringe body to enrich the 4 proteins simultaneously. Extra washing steps are applied to purify the 4 proteins. The target to be enriched or purified can also be nucleic acids or other analytes of interest.

Other Applications of MobileArray™ Device—

The above examples are only some of the applications of the MobileArray™ device, system and method to perform multiplex ELISAs, multiplex target enrichment or purification. Based on the ELISAs shown in FIG. 13, the MobileArray™ device and method to perform ELISA can be adapted to further variations. Many variations of enrichment or purification process using strips can also be designed. Analytes or targets of interest for MobileArray™ device can be protein, nucleic acids, bacteria, virus, cell or other molecules or particles that can form interaction on the surface of beads. Also, assays can be developed using variations of the MobileArray™ device, such as colored beads, or beads made of, or made to include computer chips or other electronic devices, the strips fitting tubes, 48-well plates, or other variations. MobileArray™ device can also be integrated in any automated processes whenever desired.

It will be appreciated by those skilled in the art that changes could be made to the embodiments described above without departing from the broad inventive concept thereof. It is understood, therefore, that this invention is not limited only to the particular embodiments disclosed, but it is also intended to cover modifications within the spirit and scope of the present invention. It is to be understood that this invention is not limited to the specific dimensions or examples used to explain this invention. It is to be understood that this invention is not limited to the use of 96-well microplates or 8-well strips, which are used as examples to describe the invention. It is also to be understood that the dimensions can be modified so as to optimize the current invention. It is to be understood further that modification of the device and its components may be adaptable to different uses, etc. Moreover, it is to be understood that the terminology or expressions used herein are for the purpose of describing particular embodiments only and are not intended to limit the scope of the present invention. It is also to be understood that the drawings are not to the scale of the actual device, and they are mainly used to provide some visual representations of the actual device. Unless defined otherwise, all technical and scientific terms used herein have the same meanings as commonly understood by the current scientific community.

What is claimed is:

1. A system comprising at least a first strip and a second strip for use in multiplex analyte analyses, enrichment or purification, each strip comprising a bar member, a plurality of spaced-apart rod members extending from the bar member, and a plurality of macro beads, each macro bead being attached to a respective one of the rod members, the bar member having a length equal to or longer than the width of a device with which the strip is capable of being used, a width of the bar member and a width of each rod member being the same, each macro bead having a surface that can accept a coating of a substance, which when subjected to a procedure, can interact or react with an analyte and provide a result of analysis, enrichment or purification for the analyte, wherein the bar member, the plurality of spaced-apart rod members and the plurality of macro beads are unitarily formed, and wherein positions of the plurality of macro beads of the first strip are shifted relative to positions of the macro beads of the second strip, the shift in positions being sufficient to allow at least one of the macro beads from the first strip and at least one of the macro beads from the second strip to be located in a single well of a device to mix with a sample provided in the single well so as to enable the multiplex analyte analyses.

2. A device for supporting a plurality of strips according to claim 1, wherein the device comprises a frame with a central opening, the frame having slots or ridges aligned and formed in opposite top surfaces of the frame for supporting the strips in an aligned manner.

3. A device according to claim 2, the device further comprising a divider cluster that fits within the central opening of the frame, the divider cluster comprising divider members extending from a bottom surface of the divider cluster, the divider members being aligned and spaced to separate groups of strips based on a distance corresponding to walls dividing wells of the device with which the strips are intended to be used, such that the macro beads on adjacent groups of strips stay in a format of columns or rows when the macro beads are retained on the frame and are not in the wells of the device.

4. A device according to claim 3, the device further comprising a top plate having dimensions to overlie the divider cluster and the frame, and fasteners to fasten together the top plate to the frame such that the frame, any strips supported by the frame, the divider cluster and the top plate are movable as an integrated unit.

5. The system of claim 1, each strip further comprising a labeling area at or adjacent to at least one end of the bar member.

6. The system of claim 1, each strip further comprising a plurality of semi-rigid filaments, each macro bead being attached to a respective one of the rod members by a respective one of the semi-rigid filaments.

7. A method for analyzing, enriching or purifying at least one analyte, the method comprising coating the at least one macro bead on at least one strip of claim 1 with the substance, subjecting the at least one coated bead to an analyte that may interact or react with the substance on the at least one bead, and analyzing the analyte subjected to the at least one coated bead to provide the result.

8. The method according to claim 7, wherein at least two analytes are analyzed, enriched or purified in a multiplex manner.

9. The method according to claim 7, wherein the method is integrated with an automated process for the analysis, purification or enrichment.

* * * * *